(12) United States Patent
Bartels et al.

(10) Patent No.: US 10,875,854 B2
(45) Date of Patent: Dec. 29, 2020

(54) TRIAZOLOPYRIDINES

(71) Applicant: Hoffmann-La Roche Inc., Little Falls, NJ (US)

(72) Inventors: Bjoern Bartels, Basel (CH); Roland Jakob-Roetne, Basel (CH); Anja Limberg, Basel (CH); Werner Neidhart, Basel (CH); Hasane Ratni, Basel (CH); Rosa Maria Rodriguez Sarmiento, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/224,507

(22) Filed: Dec. 18, 2018

(65) Prior Publication Data

US 2019/0194183 A1 Jun. 27, 2019

Related U.S. Application Data

(63) Continuation of application No. PCT/EP2017/065617, filed on Jun. 26, 2017.

(30) Foreign Application Priority Data

Jun. 27, 2016 (EP) ..................... 16176435

(51) Int. Cl.
 *C07D 451/04* (2006.01)
 *C07D 471/04* (2006.01)
 *A61P 25/28* (2006.01)

(52) U.S. Cl.
 CPC ............ *C07D 451/04* (2013.01); *A61P 25/28* (2018.01); *C07D 471/04* (2013.01)

(58) Field of Classification Search
 CPC ...... C07D 451/04; C07D 471/04; A61P 25/28
 (Continued)

(56) References Cited

U.S. PATENT DOCUMENTS 8,486,967 B2 * 7/2013 Baumann ............. C07D 401/14
 514/303
8,703,763 B2 * 4/2014 Baumann ............. C07D 451/04
 514/217.04

(Continued)

FOREIGN PATENT DOCUMENTS

WO 2011/092272 A1 4/2011
WO WO2011101304 * 8/2011
 (Continued)

OTHER PUBLICATIONS

Crump; "Development and Mechanism of γ-Secretase Modulators for Alzheimer's Disease", Biochemistry 2013, 52, 3197-3216. doi:10.1021/bi400377p (Year: 2013).*

(Continued)

Primary Examiner — Daniel R Carcanague
(74) Attorney, Agent, or Firm — Genentech, Inc.; Richard G.A. Bone

(57) ABSTRACT

The present invention relates to compounds of formula

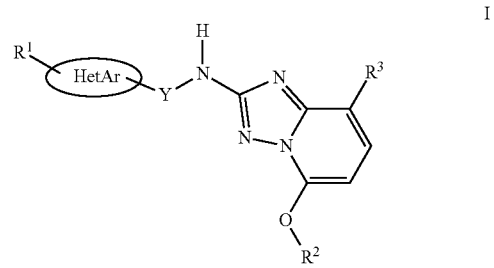

wherein
HetAr is a five or six membered hetaryl group, containing one, two or three heteroatoms, selected from N, O or S;
$R^1$ is hydrogen, lower alkyl, lower alkyl substituted by halogen, halogen or lower alkoxy;
$R^2$ is lower alkyl substituted by halogen;
$R^3$ is hydrogen, lower alkyl substituted by halogen, lower alkyl or lower alkyl substituted by hydroxy;
Y is

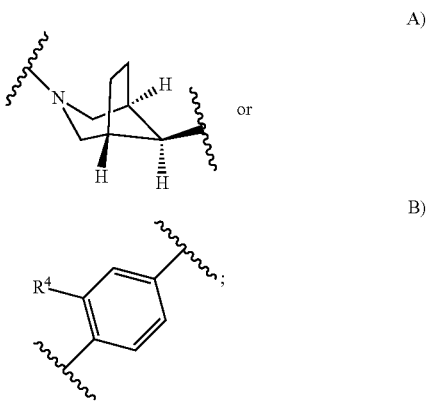

$R^4$ is lower alkoxy, lower alkoxy substituted by halogen or CN;
or to pharmaceutically active acid addition salts thereof, to racemic mixtures or to its corresponding enantiomers and/or optical isomers and/or stereoisomers thereof. The compounds may be used for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome.

8 Claims, No Drawings

(58) Field of Classification Search
USPC .................................................... 548/262.4
See application file for complete search history.

(56) References Cited

U.S. PATENT DOCUMENTS

| | | | | |
|---|---|---|---|---|
| 10,562,903 | B2* | 2/2020 | Bartels | ................ C07D 487/04 |
| 10,730,881 | B2* | 8/2020 | Bartels | ................ C07D 487/04 |
| 2011/0190269 | A1* | 8/2011 | Baumann | ............ C07D 471/04 514/217.07 |
| 2012/0295901 | A1* | 11/2012 | De Cleyn | ............ C07D 401/12 514/230.5 |
| 2015/0183790 | A1* | 7/2015 | Whittaker | ............ C07D 471/04 514/230.5 |
| 2018/0237432 | A1* | 8/2018 | Baumann | ................ A61P 25/28 |
| 2019/0010156 | A1* | 1/2019 | Bartels | ................... A61P 25/28 |
| 2019/0177329 | A1* | 6/2019 | Bartels | ................ C07D 487/04 |
| 2019/0233427 | A1* | 8/2019 | Bartels | ................ C07D 487/04 |
| 2019/0284191 | A1* | 9/2019 | Bartels | ................ C07D 487/04 |
| 2020/0031831 | A1* | 1/2020 | Bartels | ................... A61P 25/00 |

FOREIGN PATENT DOCUMENTS

| | | | | |
|---|---|---|---|---|
| WO | 2012/116965 | A1 | 7/2012 | |
| WO | WO2012116965 | | * 9/2012 | |
| WO | WO-2017042114 | A1 * | 3/2017 | ............. A61P 25/28 |
| WO | WO-2017097728 | A1 * | 6/2017 | ............. A61P 25/28 |
| WO | WO-2018060300 | A1 * | 4/2018 | ........... C07D 519/00 |
| WO | WO-2018065340 | A1 * | 4/2018 | ........... C07D 487/04 |
| WO | WO-2018083050 | A1 * | 5/2018 | ........... C07D 487/04 |
| ZA | WO2011092272 | | * 8/2011 | |

OTHER PUBLICATIONS

Golde; "γ-Secretase inhibitors and modulators", Biochimica et Biophysica Acta 1828 (2013) 2898-2907. doi:10.1016/j.bbamem.2013.06.005 (Year: 2013).*

Reitz; "Alzheimer's Disease and the Amyloid Cascade Hypothesis: A Critical Review", International journal of Alzheimer's disease, 2012, Article ID 369808, 11 pages. doi:10.1155/2012/369808 (Year: 2012).*

ISR and Written Opinion for PCT/EP2017/065617 (dated Aug. 4, 2017).

International Preliminary Report on Patentability—PCT/EP2017/065617 (dated Jan. 10, 2019).

* cited by examiner

TRIAZOLOPYRIDINES

CROSS-REFERENCE TO RELATED APPLICATIONS

This application is a continuation of, and claims priority to, International Patent Application No. PCT/EP2017/065617, filed on Jun. 26, 2017. This application also claims priority to European Patent Application No. 16176435.2, filed on Jun. 27, 2016. The entire contents of each of the above patent applications are hereby incorporated by reference.

The present invention relates to compounds of formula

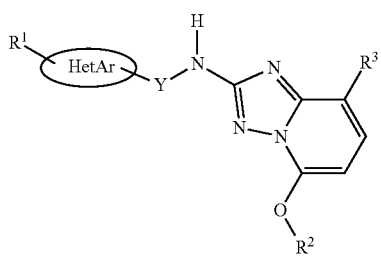

I wherein
HetAr is a five or six membered hetaryl group, containing one, two or three heteroatoms, selected from N, O or S;
$R^1$ is hydrogen, lower alkyl, lower alkyl substituted by halogen, halogen or lower alkoxy;
$R^2$ is lower alkyl substituted by halogen;
$R^3$ is hydrogen, lower alkyl substituted by halogen, lower alkyl or lower alkyl substituted by hydroxy;
Y is

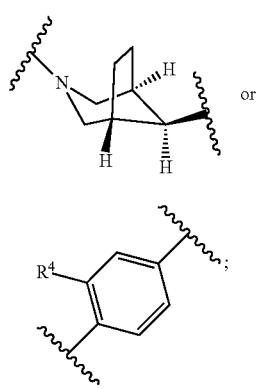

A)

or

B)

$R^4$ is lower alkoxy, lower alkoxy substituted by halogen or CN;
or to pharmaceutically active acid addition salts thereof, to racemic mixtures or to its corresponding enantiomers and/or optical isomers and/or stereoisomers thereof.

Now it has been found that the present compounds of formula I are modulators of γ-secretase, they may be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Alzheimer's disease (AD) is the most common cause of dementia in later life. Pathologically, AD is characterized by the deposition of amyloid in extracellular plaques and intracellular neurofibrillary tangles in the brain. The amyloid plaques are mainly composed of amyloid peptides (Aβ peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Aβ peptides are derived from the same domain of the APP.

Aβ peptides are produced from APP through the sequential action of two proteolytic enzymes termed β- and γ-secretase. β-Secretase cleaves first in the extracellular domain of APP just outside of the trans-membrane domain (TM) to produce a C-terminal fragment of APP (CTFβ) containing the TM- and cytoplasmatic domain. CTFβ is the substrate for γ-secretase which cleaves at several adjacent positions within the TM to produce the Aβ peptides and the cytoplasmic fragment. Various proteolytic cleavages mediated by γ-secretase result in Aβ peptides of different chain length, e.g. Aβ38, Aβ40 and Aβ42. The latter one is regarded to be the more pathogenic amyloid peptide because of its strong tendency to form neurotoxic aggregates.

The β-secretase is a typical aspartyl protease. The γ-secretase is a high molecular weight complex that consists of four essential subunits: Presenilin (PS, including PS1 and PS2), nicastrin, anterior pharynx defective 1 (APH-1), and presenilin enhancer 2 (PEN-2). The atomic structure of human γ-secretase at 3.4 Å resolution has been published (X. Bai, C. Yan, G. Yang, P. Lu, D. Ma, L. Sun, R. Zhou, S. H. W. Scheres, Y. Shi, Nature 2015, doi:10.1038/nature14892). The presenilins are bearing the catalytic site and represent a group of atypical aspartyl proteases which cleave their substrates within the TM of and which are themselves polytopic membrane proteins. The other essential components of γ-secretase, nicastrin and the products of the aph1 and pen-2 genes are believed to be responsible for substrate recognition and recruitment. Proven substrates for γ-secretase are APP and the proteins of the Notch receptor family, however, γ-secretase has a loose substrate specificity and many further membrane proteins unrelated to APP and Notch have been reported to be cleaved by the γ-secretase in vitro.

The γ-secretase activity is absolutely required for the production of Aβ peptides. This has been shown both by genetic means, i.e., ablation of the presenilin genes and by low-molecular-weight inhibitory compounds. According to the amyloid cascade hypothesis for AD the production and deposition of Aβ is the ultimate cause for the disease. Therefore, it was believed that selective and potent inhibition of γ-secretase might be useful for the prevention and treatment of AD.

An alternative mode of treatment is the modulation of the γ-secretase activity which results in a selective reduction of the Aβ42 production. This will lead in an increase of shorter Aβ isoforms, such as Aβ38, Aβ37 or others, which have no or reduced capability for aggregation and plaque formation, and are not or less neurotoxic. Compounds which show this effect on modulating γ-secretase activity include certain non-steroidal anti-inflammatory drugs (NSAIDs) and related analogues (Weggen et al. Nature, 414 (2001) 212-16).

Thus, the compounds of this invention will be useful for the treatment or prevention of a disease associated with the deposition of β-amyloid in the brain, in particular Alzheimer's disease, and other diseases such as cerebral amyloid angiopathy, hereditary cerebral hemorrhage with amyloidosis, Dutch-type (HCHWA-D), multi-infarct dementia, dementia pugilistica and Down syndrome.

Numerous documents describe the current knowledge on γ-secretase modulation, for example the following publications:

Morihara et al, J. Neurochem., 83 (2002) 1009-12
Jantzen et al, J. Neuroscience, 22 (2002) 226-54
Takahashi et al, J. Biol. Chem., 278 (2003) 18644-70
Beher et al, J. Biol. Chem. 279 (2004) 43419-26
Lleo et al, Nature Med. 10 (2004) 1065-6
Kukar et al, Nature Med. 11 (2005) 545-50
Perretto et al, J. Med. Chem. 48 (2005) 5705-20
Clarke et al, J. Biol. Chem. 281 (2006) 31279-89
Stock et al, Bioorg. Med. Chem. Lett. 16 (2006) 2219-2223
Narlawar et al, J. Med. Chem. 49 (2006) 7588-91
Ebke et al, J. Biol. Chem., 286 (2011) 37181-86
Hall et al, Progress in Med. Chem., 53 (2014) 101-145

The following definitions for compounds of formula I are used:

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkyl substituted by halogen" denotes an alkyl group as defined above, wherein at least one hydrogen atom is replaced by halogen, for example $CF_3$, $CHF_2$, $CH_2F$, $CHFCF_3$, $CH_2CHF_2$, $CH_2CH_2F$, $CH_2C(CH_3)_2CF_3$, $CH_2CF_2CF_3$, $CH(CF_3)_2$, $CH_2CF_3$, $(CH_2)_2CF_3$, $(CH_2)_3CF_3$, $CH(CH_3)CF_3$, $CF_2CF_3$, and the like.

As used herein, the term "lower alkoxy" denotes a saturated straight- or branched-chain group containing from 1 to 7 carbon atoms, for example, methyl, ethyl, propyl, isopropyl, n-butyl, i-butyl, 2-butyl, t-butyl and the like, which group is connected via an O-group.

As used herein, the term "lower alkoxy substituted by halogen" denotes an alkoxy group as defined above, wherein at least one hydrogen atom is replaced by halogen, for example $OCF_3$, $OCHF_2$, $OCH_2F$, $OCHFCF_3$, $OCH_2CHF_2$, $OCH_2CH_2F$, $OCH_2C(CH_3)_2CF_3$, $OCH_2CF_2CF_3$, $OCH(CF_3)_2$, $OCH_2CF_3$, $O(CH_2)_2CF_3$, $O(CH_2)_3CF_3$, $OCH(CH_3)CF_3$, $OCF_2CF_3$, and the like.

As used herein, the term "lower alkyl substituted by hydroxy" denotes an alkyl group as defined above, wherein at least one hydrogen atom is replaced by hydroxy, for example $C(CH_3)_2OH$.

The term "halogen" denotes chlorine, iodine, fluorine and bromine.

The term "five or six membered hetaryl group, containing one, two or three heteroatoms, selected from N, O or S" is selected from the group consisting of

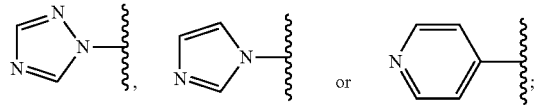

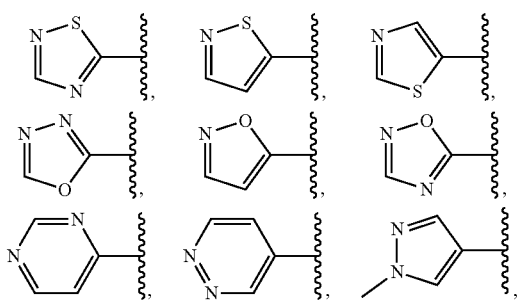

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Objects of the present invention are compounds of formula I, the use of such compounds for the preparation of medicaments for the treatment of Alzheimer's disease, cerebral amyloid angiopathy, hereditary cerebral hemorrhage with amyloidosis, Dutch-type (HCHWA-D), multi-infarct dementia, dementia pugilistica or Down syndrome, their manufacture and medicaments based on a compound of formula I in accordance with the invention.

Further objects of the invention are all forms of optically pure enantiomers, racemates or diastereomeric mixtures for compounds of formula I.

One object of the invention is a compound of formula IA

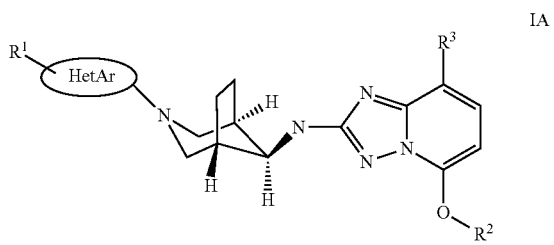

wherein

HetAr is a five or six membered hetaryl group, containing one, two or three heteroatoms, selected from N, O or S;

$R^1$ is hydrogen, lower alkyl, lower alkyl substituted by halogen, halogen, or lower alkoxy;

$R^2$ is lower alkyl substituted by halogen;

$R^3$ is hydrogen, lower alkyl substituted by halogen, lower alkyl or lower alkyl substituted by hydroxy;

or pharmaceutically active acid addition salts thereof, racemic mixtures or its corresponding enantiomers and/or optical isomers and/or stereoisomers thereof, for example the following compounds 5-(2,2,2-Trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine N-((8 endo)-3-(3-methylisothiazol-5-yl)-3-azabicyclo[3.2.1]octan-8-yl)-5-(2,2,2-trifluoroethoxy)-[1,2,4]triazolo[1,5-a]pyridin-2-amine 8-methyl-5-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine 8-methyl-N-((8 endo)-3-(6-methylpyrimidin-4-yl)-3-azabicyclo[3.2.1]octan-8-yl)-5-(2,2,2-trifluoroethoxy)-[1,2,4]triazolo[1,5-a]pyridin-2-amine N-((8 endo)-3-(2-chloropyridin-4-yl)-3-azabicyclo[3.2.1]
 octan-8-yl)-8-methyl-5-(2,2,2-trifluoroethoxy)-[1,2,4]tri-
 azolo[1,5-a]pyridin-2-amine N-((8 endo)-3-(2-methoxypyridin-4-yl)-3-azabicyclo[3.2.1]
 octan-8-yl)-8-methyl-5-(2,2,2-trifluoroethoxy)-[1,2,4]tri-
 azolo[1,5-a]pyridin-2-amine N-((8 endo)-3-(6-chloropyridazin-4-yl)-3-azabicyclo[3.2.1]
 octan-8-yl)-8-methyl-5-(2,2,2-trifluoroethoxy)-[1,2,4]tri-
 azolo[1,5-a]pyridin-2-amine 2-(5-(2,2,2-trifluoroethoxy)-2-(((8 endo)-3-(2-(trifluorom-
 ethyl)pyridin-4-yl)-3-azabicyclo[3.2.1]octan-8-yl)
 amino)-[1,2,4]triazolo[1,5-a]pyridin-8-yl)propan-2-ol 2-(2-(((8 endo)-3-(6-methylpyrimidin-4-yl)-3-azabicyclo
 [3.2.1]octan-8-yl)amino)-5-(2,2,2-trifluoroethoxy)-[1,2,
 4]triazolo[1,5-a]pyridin-8-yl)propan-2-ol 8-isopropyl-5-(2,2,2-trifluoroethoxy)-N-((8 endo)-3-(2-(tri-
 fluoromethyl)pyridin-4-yl)-3-azabicyclo[3.2.1]octan-8-
 yl)-[1,2,4]triazolo[1,5-a]pyridin-2-amine 8-isopropyl-N-((8 endo)-3-(6-methylpyrimidin-4-yl)-3-
 azabicyclo[3.2.1]octan-8-yl)-5-(2,2,2-trifluoroethoxy)-
 [1,2,4]triazolo[1,5-a]pyridin-2-amine N-((8 endo)-3-(2-chloropyridin-4-yl)-3-azabicyclo[3.2.1]
 octan-8-yl)-8-isopropyl-5-(2,2,2-trifluoroethoxy)-[1,2,4]
 triazolo[1,5-a]pyridin-2-amine 8-Isopropyl-N-((8 endo)-3-(2-methoxypyridin-4-yl)-3-
 azabicyclo[3.2.1]octan-8-yl)-5-(2,2,2-trifluoroethoxy)-
 [1,2,4]triazolo[1,5-a]pyridin-2-amine N-((8 endo)-3-(6-chloropyridazin-4-yl)-3-azabicyclo[3.2.1]
 octan-8-yl)-8-isopropyl-5-(2,2,2-trifluoroethoxy)-[1,2,4]
 triazolo[1,5-a]pyridin-2-amine 8-isopropyl-N-((8 endo)-3-(6-methoxypyridazin-4-yl)-3-
 azabicyclo[3.2.1]octan-8-yl)-5-(2,2,2-trifluoroethoxy)-
 [1,2,4]triazolo[1,5-a]pyridin-2-amine 8-Isopropyl-N-((8 endo)-3-(3-methyl-1,2,4-oxadiazol-5-yl)-
 3-azabicyclo[3.2.1]octan-8-yl)-5-(2,2,2-trifluoroethoxy)-
 [1,2,4]triazolo[1,5-a]pyridin-2-amine 2-[2-[[(8 endo)-3-(6-methylpyrimidin-4-yl)-3-azabicyclo
 [3.2.1]octan-8-yl]amino]-5-[(1S)-2,2,2-trifluoro-1-
 methyl-ethoxy]-[1,2,4]triazolo[1,5-a]pyridin-8-yl]pro-
 pan-2-ol 2-[2-[[(8 endo)-3-6-chloropyridazin-4-yl)-3-azabicyclo
 [3.2.1]octan-8-yl]amino]-5-[(1S)-2,2,2-trifluoro-1-
 methyl-ethoxy]-[1,2,4]triazolo[1,5-a]pyridin-8-yl]pro-
 pan-2-ol 8-isopropyl-N-((8 endo)-3-2-methoxypyridin-4-yl)-3-azabi-
 cyclo[3.2.1]octan-8-yl)-5-(((S)-1,1,1-trifluoropropan-2-
 yl)oxy)-[1,2,4]triazolo[1,5-a]-2-amine 8-isopropyl-N-((8 endo)-3-6-methoxypyridazin-4-yl)-3-
 azabicyclo[3.2.1]octan-8-yl)-5-(((S)-1,1,1-trifluoropro-
 pan-2-yl)oxy)-[1,2,4]triazolo[1,5-a]pyridin-2-amine N-((8 endo)-3-6-chloropyridazin-4-yl)-3-azabicyclo[3.2.1]
 octan-8-yl)-8-isopropyl-5-(((S)-1,1,1-trifluoropropan-2-
 yl)oxy)-[1,2,4]triazolo[1,5-a]-2-amine 8-isopropyl-N-[(8 endo)-3-3-methyl-1,2,4-oxadiazol-5-yl)-
 3-azabicyclo[3.2.1]octan-8-yl]-5-[(1S)-2,2,2-trifluoro-1-
 methyl-ethoxy]-[1,2,4]triazolo[1,5-a]pyridin-2-amine or 8-isopropyl-N-[(8 endo)-3-5-methyl-1,3,4-oxadiazol-2-yl)-
 3-azabicyclo[3.2.1]octan-8-yl]-5-[(1S)-2,2,2-trifluoro-1-
 methyl-ethoxy]-[1,2,4]triazolo[1,5-a]pyridin-2-amine.

One object of the invention is a compound of formula IB

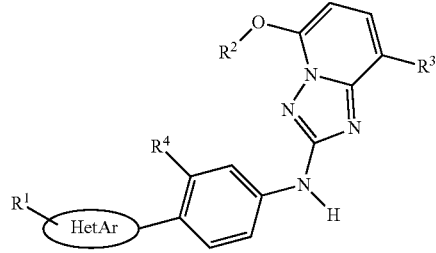

wherein
HetAr is a five or six membered hetaryl group, containing one, two or three heteroatoms, selected from N, O or S;
$R^1$ is hydrogen, lower alkyl, lower alkyl substituted by halogen, halogen, or lower alkoxy;
$R^2$ is lower alkyl substituted by halogen;
$R^3$ is hydrogen, lower alkyl substituted by halogen, lower alkyl or lower alkyl substituted by hydroxy;
$R^4$ is lower alkoxy, lower alkoxy substituted by halogen or CN;
or pharmaceutically active acid addition salts thereof, racemic mixtures or its corresponding enantiomers and/or optical isomers and/or stereoisomers thereof, for example the following compounds 2-(2-((3-difluoromethoxy)-4-(3-methyl-1H-1,2,4-triazol-1-yl)phenyl)amino)-5-(2,2,2-trifluoroethoxy)-[1,2,4]triazolo[1,5-a]pyridin-8-yl)propan-2-ol N-(3-difluoromethoxy)-4-(3-methyl-1H-1,2,4-triazol-1-yl)phenyl)-8-isopropyl-5-(2,2,2-trifluoroethoxy)-[1,2,4]triazolo[1,5-a]pyridin-2-amine 8-Isopropyl-N-(3-methoxy-4-(3-methyl-1H-1,2,4-triazol-1-yl)phenyl)-5-(2,2,2-trifluoroethoxy)-[1,2,4]triazolo[1,5-a]pyridin-2-amine 5-((8-isopropyl-5-(2,2,2-trifluoroethoxy)-[1,2,4]triazolo[1,5-a]pyridin-2-yl)amino)-2-(4-methyl-1H-imidazol-1-yl)benzonitrile 8-isopropyl-N-(3-methoxy-4-(2-methylpyridin-4-yl)phenyl)-5-(2,2,2-trifluoroethoxy)-[1,2,4]triazolo[1,5-a]pyridin-2-amine 2-[2-[3-methoxy-4-(3-methyl-1,2,4-triazol-1-yl)anilino]-5-[(1S)-2,2,2-trifluoro-1-methyl-ethoxy]-[1,2,4]triazolo[1,5-a]pyridin-8-yl]propan-2-ol 2-[2-[4-(4-chloroimidazol-1-yl)-3-methoxy-anilino]-5-[(1S)-2,2,2-trifluoro-1-methyl-ethoxy]-[1,2,4]triazolo[1,5-a]pyridin-8-yl]propan-2-ol 2-[2-[4-(3-chloro-1,2,4-triazol-1-yl)-3-methoxy-anilino]-5-[(1S)-2,2,2-trifluoro-1-methyl-ethoxy]-[1,2,4]triazolo[1,5-a]pyridin-8-yl]propan-2-ol 5-[[8-(1-hydroxy-1-[(1S)-2,2,2-trifluoro-1-methyl-ethoxy]-[1,2,4]triazolo[1,5-a]pyridin-2-yl]amino]-2-(4-methyl-imidazol-1-yl)benzonitrile 8-isopropyl-N-[3-methoxy-4-(3-methyl-1,2,4-triazol-1-yl)phenyl]-5-[(1S)-2,2,2-trifluoro-1-methyl-ethoxy]-[1,2,4]triazolo[1,5-a]pyridin-2-amine N-[3-methoxy-4-(3-methyl-1,2,4-triazol-1-yl)phenyl]-8-(trifluoromethyl)-5-[(1S)-2,2,2-trifluoro-1-methyl-ethoxy]-[1,2,4]triazolo[1,5-a]pyridin-2-amine or N-[4-(4-chloroimidazol-1-yl)-3-methoxy-phenyl]-8-(trifluoromethyl)-5-[(1S)-2,2,2-trifluoro-1-methyl-ethoxy]-[1,2,4]triazolo[1,5-a]pyridin-2-amine.

The present compound may be prepared as described below, by schemes 1-6 and by examples 1-35.

The present compounds of formula I and their pharmaceutically acceptable salts can be prepared by methods known in the art, for example, by processes described below, which processes comprise a) reacting a compound of formula

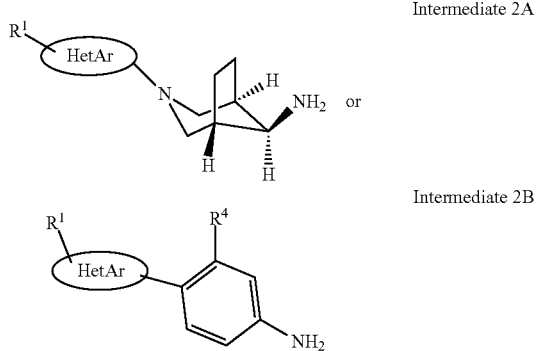

Intermediate 2A or

Intermediate 2B with a compound of intermediate 3

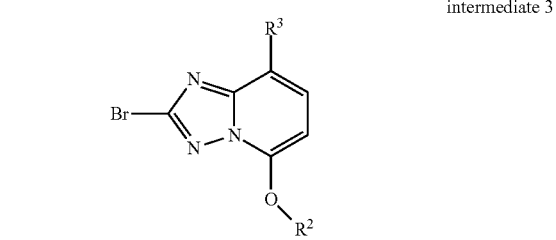

intermediate 3 to a compound of formula

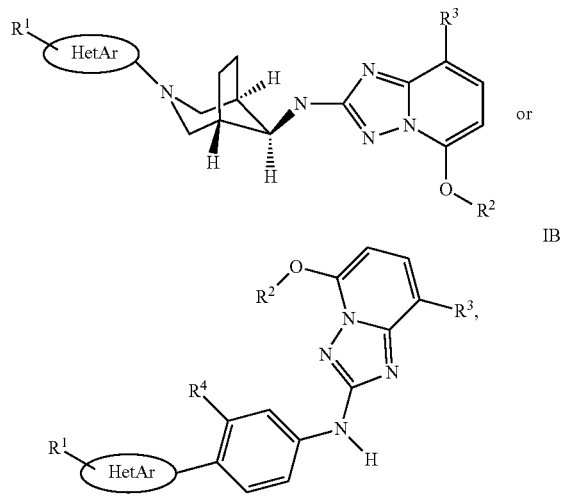

IA or

IB wherein the substituents have the meaning as described above, and, if desired, converting the compounds obtained into pharmaceutically acceptable acid addition salts;

The preparation of compounds of formula I of the present invention may be carried out in sequential or convergent synthetic routes. Syntheses of the compounds of the invention are shown in the following schemes. The capability required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in the examples, or by methods known in the art.

Particularly, compounds of formula I can be prepared following standard methods in accordance with any of the Schemes 1 to 8.

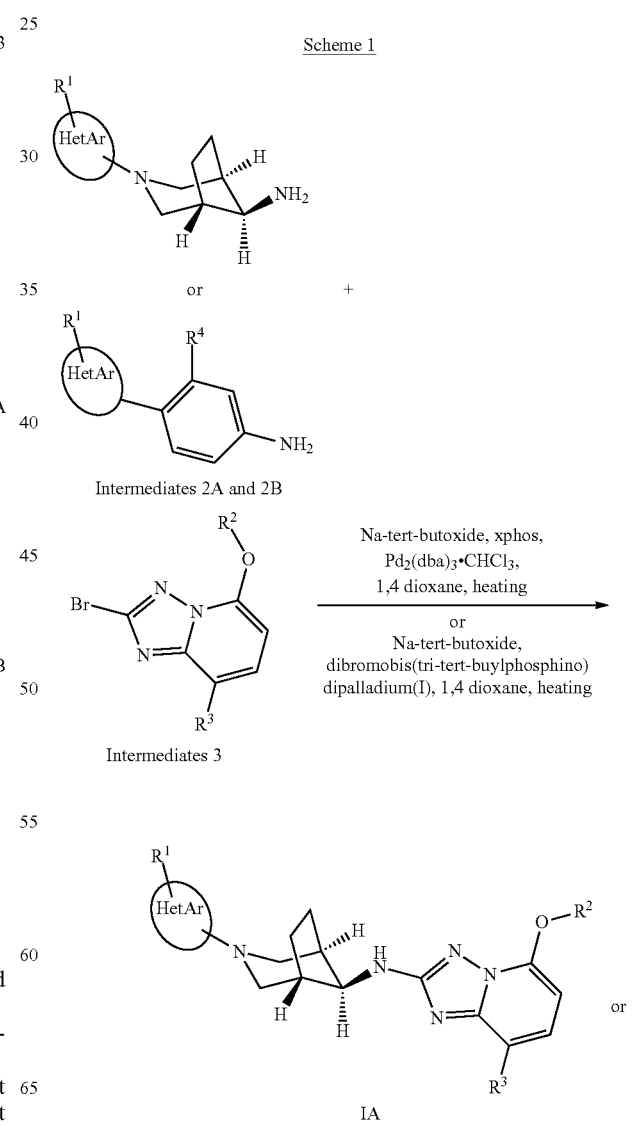

Scheme 1

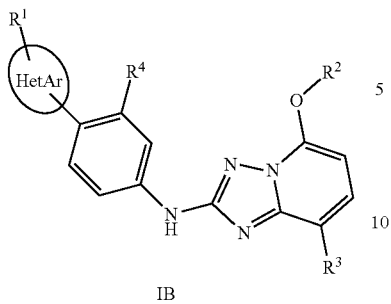

IB

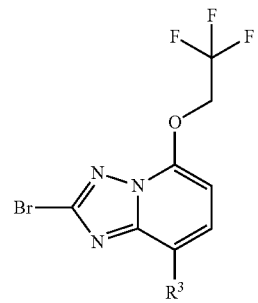

R³ = H: Intermediate 3.1
R³ = Me: Intermediate 3.2

According to Scheme 1, the present compounds of formula IA and IB and their pharmaceutically acceptable salts can be prepared by coupling of amines of general formula 2A and 2B and bromides of general formula 3. This reaction can be accomplished using generally known procedures, e.g. displacement reactions under thermal conditions or under catalytic conditions (like e.g. palladium(0) catalysis).

Bromo-triazolopyridines intermediates of general formula 3.1 or 3.2, which can be used as starting materials for the preparation of compounds of formula IA or IB can be prepared as described below.

Scheme 2: Intermediate 3.1 and 3.2

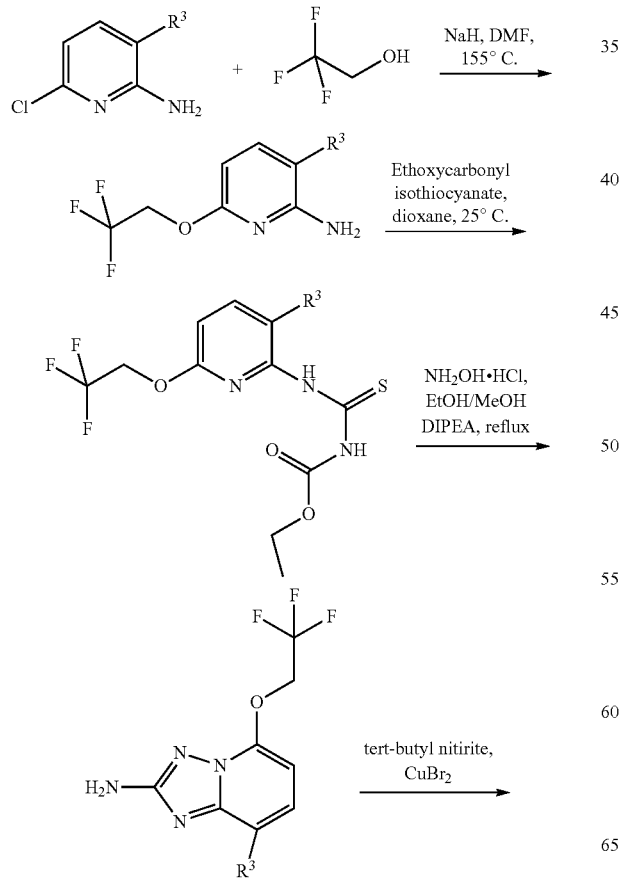

Scheme 3: Intermediate 3.3 and 3.4

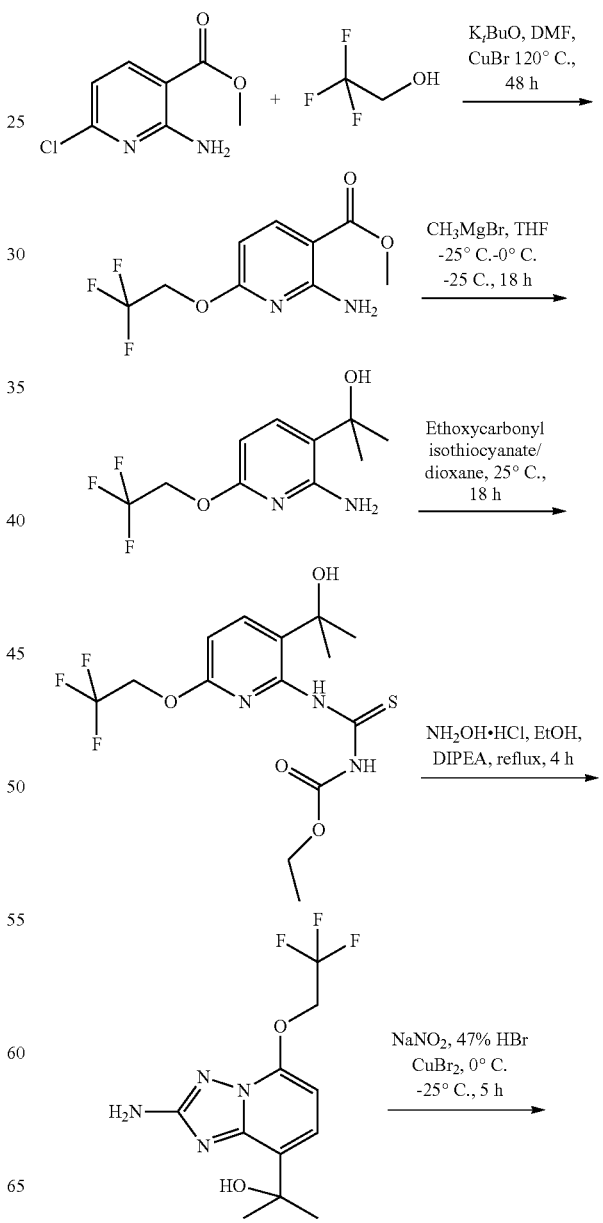

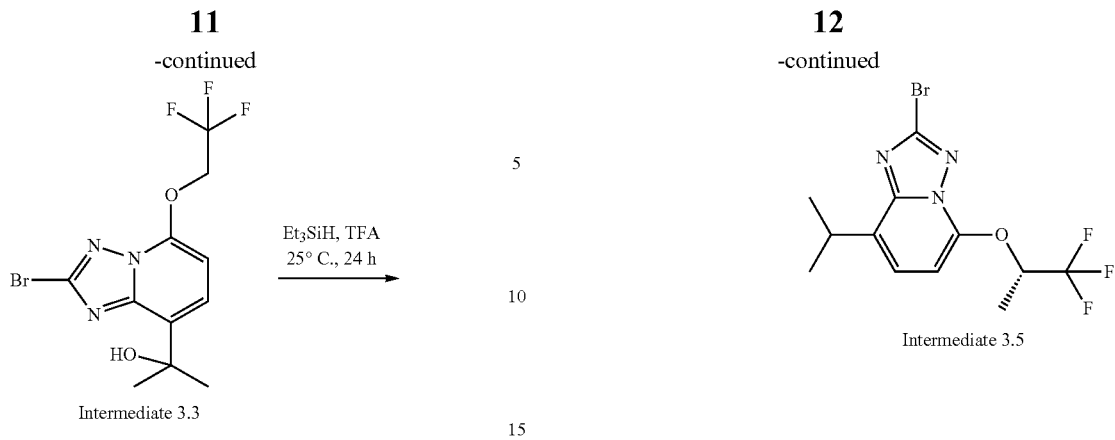
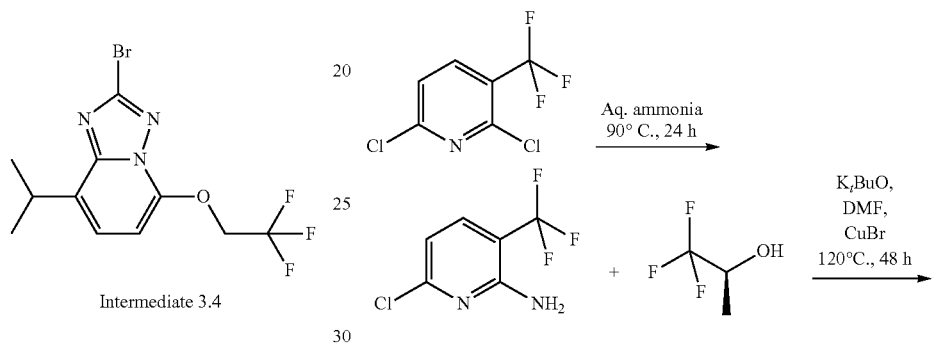
Scheme 4: Intermediate 3.5 and 3.6
The intermediates 3.5 and 3.6 were prepared employing the same sequence as described for intermediates 3.3 and 3.4 (Scheme 3) from (2S)-1,1,1-trifluoropropan-2-ol instead of 2,2,2-trifluoroethanol.
Scheme 5: Intermediate 3.7
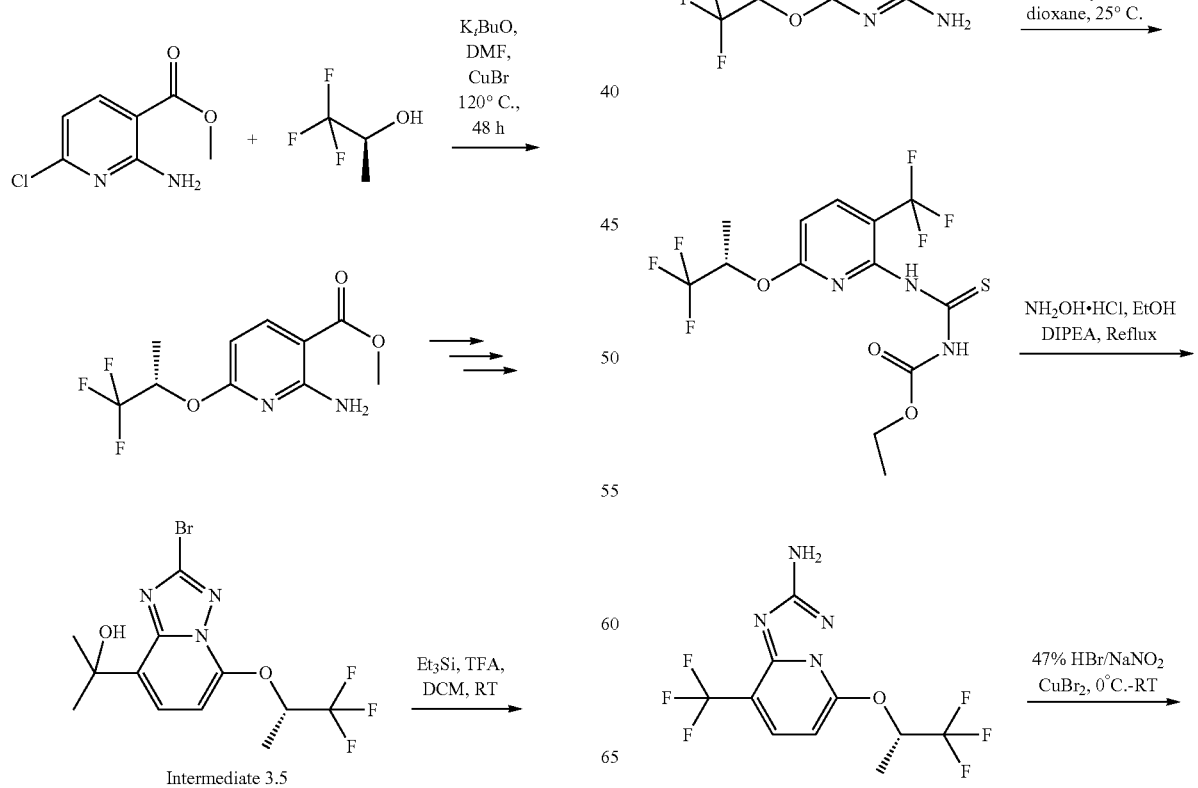

-continued

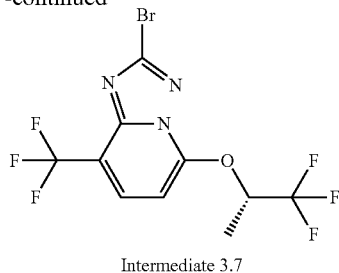

Intermediate 3.7

Synthetic access to intermediates 2A are described in scheme 6.

Scheme 6: Intermediates 2:

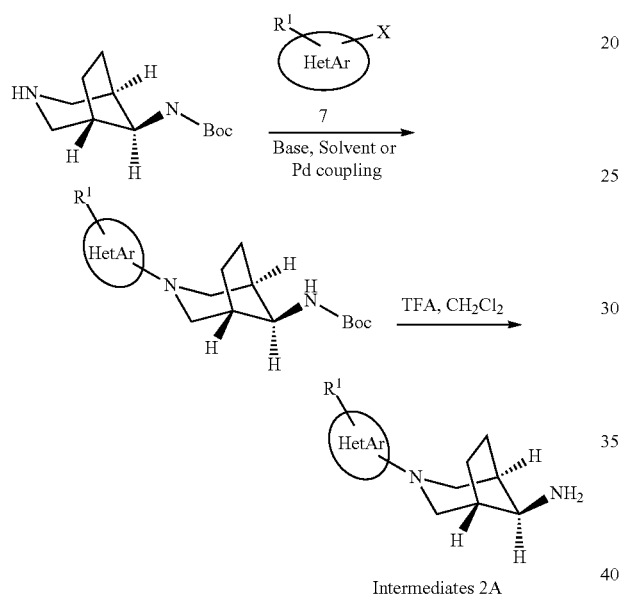

Intermediates 2A

Thus intermediates 2A can be synthesized starting from meso [(8-endo)-3-aza-bicyclo [3,2,1]oct-8-yl]-carbamic acid tert-butyl ester by protective group modifications such as the one described in WO2012116965, page 37-38. The coupling with heterocyclic halides can be accomplished under thermal conditions in a solvent such as ethanol or NMP in the presence of a base such as $Et_3N$ or by using displacement reactions under catalytic conditions (like e.g. palladium(0) or copper(II) catalysis). After de-protection with acid e.g. trifluoro acetic acid intermediates 2A can be obtained ready for coupling with intermediates 3 as described in scheme 1.

Other intermediates 2B of general formula below are either known in the literature or were prepared by standard procedures known in the art (experimental section).

Intermediates 2B

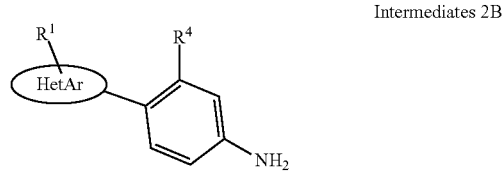

EXAMPLE 1

5-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine

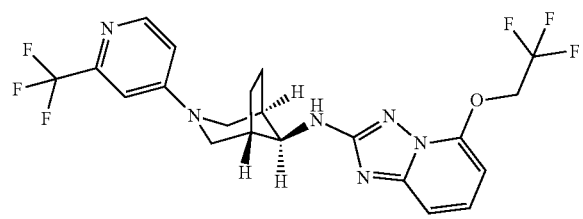 [SMILES: FC(F)(F)COc1cccc2nc(N[C@@H]3[C@@H]4CC[C@H]3CN(c3ccnc(C(F)(F)F)c3)C4)nn12]

Intermediate 3.1

2-bromo-5-(2,2,2-trifluoroethoxy)-[1,2,4]triazolo[1,5-a]pyridine

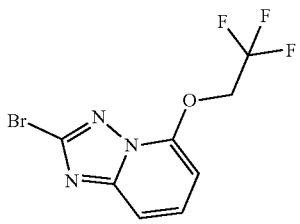 [SMILES: FC(F)(F)COc1cccc2nc(Br)nn12]

Step 1

6-(2,2,2-trifluoroethoxy)pyridin-2-amine

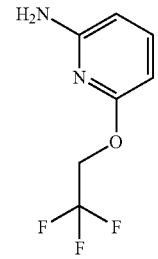 [SMILES: Nc1cccc(OCC(F)(F)F)n1]

To a suspension of NaH (60%, 340 mg, 7.8 mmol) in DMF (10 mL) at 0° C. was added drop-wise 2,2,2-trifluoroethanol (900 mg, 9 mmol) dissolved in DMF (10 ml). The mixture was stirred for 10 minutes at 0° C. and 30 minutes at RT. 6-Chloropyridine-2-amine (771 mg, 6 mmol) dissolved in DMF (10 ml) was added drop-wise to the reaction mixture followed by copper (I) bromide (8.61 mg, 60 mMol). The reaction mixture was heated at 155° C. for 3 h then cooled to RT and partitioned between 150 ml of AcOEt 120 ml of water. The organic layer was separated and washed 3 times with 50 ml of brine. The organic layer was dried over $Na_2SO_4$, filtered, the solvent was removed in vacuo and the crude product was purified by flash chromatography (silica gel 20 g, eluent 0% to 25% EtOAc in heptane) to give the desired compound as light yellow solid (344 mg. 29.8%). MS ES+ (m/z): 193 (M+H)+.

Step 2

Ethyl N-[[6-(2,2,2-trifluoroethoxy)-2-pyridyl]carbamothioyl]carbamate

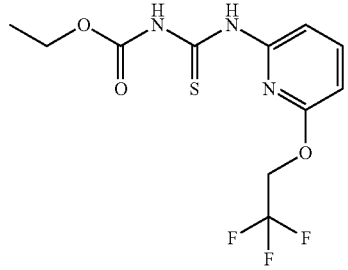 [SMILES: CCOC(=O)NC(=S)Nc1cccc(OCC(F)(F)F)n1]

6-(2,2,2-Trifluoroethoxy)pyridin-2-amine (537 mg, 2.79 mmol) in dioxane (10 ml) were treated at RT with ethoxycarbonyl-isothiocyanate (196 mg, 176 µl, 1.49 mmol). The reaction mixture was stirred at RT for 20 h, the solvent was removed in vacuo to give the desired crude product ad a semi-solid (873 mg, 96.6%) which was directly used in the subsequent reaction step.

Step 3

5-(2,2,2-Trifluoroethoxy)-[1,2,4]triazolo[1,5-a]pyridin-2-amine

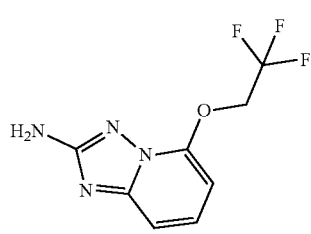 [SMILES: Nc1nc2cccc(OCC(F)(F)F)n2n1]

Ethyl N-[[6-(2,2,2-trifluoroethoxy)-2-pyridyl]carbamothioyl]carbamate (873 mg, 2.7 mmol) in a mixture of ethanol and methanol (each 6 ml) was treated at 70° C. with N-ethyldiisopropylamin (698 mg, 924 µl, 5.4 mmol) and hydroxylamin×HCl (197 mg, 2.84 mmol) and the mixture was then heated at 70° C. for 3 h. The solvent was removed in vacuo, the residue partitioned between water (50 ml) and AcOEt (50 ml). The organic layer was separated, washed with KHCO$_3$ (50 ml), tried over Na$_2$SO$_4$, filtered and the solvent was then removed in vacuo. The crude product was purified by flash chromatography (silica gel 20 g, eluent 0% to 30% EtOAc in heptane) to give the desired compound as an off-white solid (402 mg. 64.1%). MS ES+ (m/z): 233.064 (M+H)+.

Step 4

2-bromo-5-(2,2,2-trifluoroethoxy)-[1,2,4]triazolo[1,5-a]pyridine

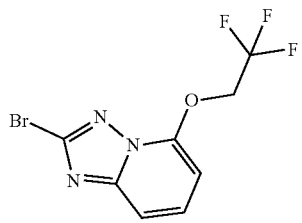 [SMILES: FC(F)(F)COc1cccc2nc(Br)nn12]

Copper (II) bromide (577 mg, 2.58 mmol) and tert-butyl nitrite (267 mg, 307 µl, 2.58 mmol) in acetonitrile (15 ml) was treated at 60° C. dropwise with 5-(2,2,2-trifluoroethoxy)-[1,2,4]triazolo[1,5-a]pyridin-2-amine (400 mg, 1.72 mmol) dissolved in acetonitrile (7 ml). The reaction was the heated further 30 minutes at 60° C. to complete the reaction. The mixture was cooled to RT, the solvent was removed in vacuo, the residue partitioned between water and AcOEt. The organic layer was separated, tried over Na$_2$SO$_4$, filtered and the solvent was then removed in vacuo. The crude product was purified by flash chromatography (silica gel 20 g, eluent 0% to 30% EtOAc in heptane) to give the desired compound as a white solid (372 mg. 72.9%). HR-MS ES+ (m/z): 295.96497 (M+H)+.

Intermediate 2.1

(8 endo)-3-(2-(trifluoromethyl)pyridin-4-yl)-3-azabicyclo[3.2.1]octan-8-amine

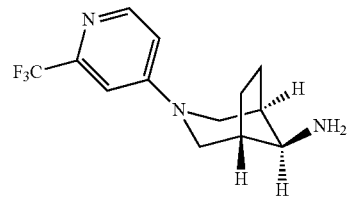 [SMILES: N[C@@H]1[C@@H]2CC[C@H]1CN(c1ccnc(C(F)(F)F)c1)C2]

Step 1

Tert-butyl N-[(8 endo)-3-(2-(trifluoromethyl)pyridin-4-yl)-3-azabicyclo[3.2.1]octan-8-yl]carbamate

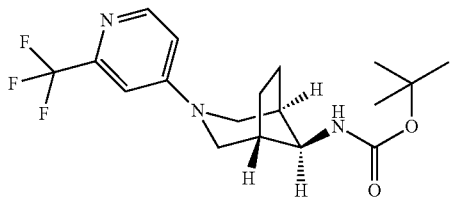 [SMILES: CC(C)(C)OC(=O)N[C@@H]1[C@@H]2CC[C@H]1CN(c1ccnc(C(F)(F)F)c1)C2]

To a solution of tert-butyl (8 endo)-3-azabicyclo[3.2.1]octan-8-ylcarbamate (1.57 g, 6.93 mmol) in NMP (11 ml) in a tube and under argon, was added DIPEA (964 mg, 1.3 ml, 7.46 mmol) followed by 4-iodo-2-(trifluoromethyl)pyridine (1.5 g, 5.33 mmol). The vial was closed under Argon and the reaction mixture was stirred over night at 150° C. TLC and LC-MS showed the reaction was complete. The reaction mixture was diluted with 30 mL H$_2$O and extracted with EtOAc (3×30 mL). The organic layers were dried over MgSO$_4$ and concentrated in vacuum. The crude material was purified by flash chromatography (silica gel 20 g, eluent 0% to 70% EtOAc in heptane) to afford the title compound (1.375 g, 69.5% yield). MS ES+ (m/z): 372.2 [(M+H)+]

Step 2

(8 endo)-3-(2-(trifluoromethyl)pyridin-4-yl)-3-azabicyclo[3.2.1]octan-8-amine

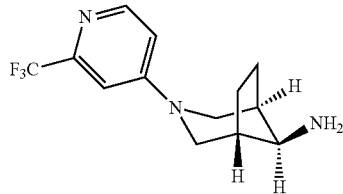 [SMILES: N[C@@H]1[C@@H]2CC[C@H]1CN(c1ccnc(C(F)(F)F)c1)C2]

The compound was prepared in analogy to example 50 (step 2, intermediate 2) using tert-butyl N-[(8 endo)-3-2-(trifluoromethyl)pyridin-4-yl)-3-azab icyclo[3.2.1]octan-8-yl]carbamate (1.049 g, 2.82 mmol) in dichloromethane in the presence of HCl 37% (1.68 g, 1.4 ml, 17 mmol). The title compound was obtained after extraction using sat NaHCO$_3$ and DCM as a light yellow solid (735 mg, 96% yield). MS ES+ (m/z): 272.2 [(M+H)+]

Step 3, Final Coupling 5-(2,2,2-Trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine

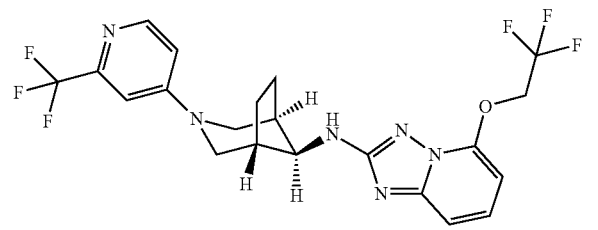 [SMILES: FC(F)(F)COc1cccc2nc(N[C@@H]3[C@@H]4CC[C@H]3CN(c3ccnc(C(F)(F)F)c3)C4)nn12]

To a solution of 2-bromo-5-(2,2,2-trifluoroethoxy)-[1,2,4]triazolo[1,5-a]pyridine (44.4 mg, 150 µmol), (8-endo)-3-(2-(trifluoromethyl)pyridin-4-yl)-3-azabicyclo[3.2.1]octan-8-amine (40.7 mg, 150 µmol) in 1,4-dioxane (2.5 ml) was added sodium tert-butoxide (29.6 mg, 307 µmol). The mixture was purged with argon for 5 minutes and dibromobis(tri-tert-butylphosphino) dipalladium(I) (11.7 mg, 15 µmol) was added. The reaction mixture was purged again with argon for 2 minutes, sealed and heated to 120° C. for 5 hours. The mixture was concentrated in vacuo and the residue purified by flash chromatography (10 g, eluent AcOEt). The title compound was obtained as a light yellow solid (28 mg, 38.4% yield). HR-MS ES+ (m/z): 487.16929 [(M+H)+]

EXAMPLE 2

N-((8 endo)-3-(3-methylisothiazol-5-yl)-3-azabicyclo[3.2.1]octan-8-yl)-5-(2,2,2-trifluoroethoxy)-[1,2,4]triazolo[1,5-a]pyridin-2-amine

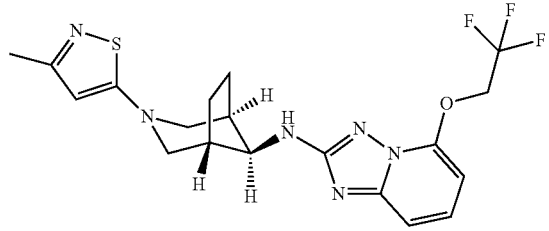 [SMILES: Cc1cc(N2C[C@H]3CC[C@@H](C2)[C@@H]3Nc2nc3cccc(OCC(F)(F)F)n3n2)sn1]

Intermediate 2.2

(8-endo)-3-(3-Methylisothiazol-5-yl)-3-azabicyclo[3.2.1]octan-8-amine

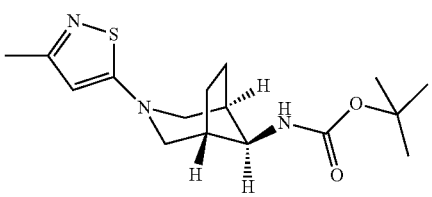 [SMILES: Cc1cc(N2C[C@H]3CC[C@@H](C2)[C@@H]3NC(=O)OC(C)(C)C)sn1]

Step 1

Tert-Butyl ((8-meso)-3-(3-Methylisothiazol-5-yl)-3-azabicyclo[3.2.1]octan-8-yl)carbamate In a 250 mL round-bottomed flask, 4-methyl-6-thioxo-3,6-dihydro-2H-1,3-thiazin-2-one (CAS 97309-82-5, 1.50 g, 9.42 mmol), tert-butyl (8-anti)-3-azabicyclo[3.2.1]octan-8-ylcarbamate (CAS 847862-26-4, 2.13 g, 9.42 mmol), 4-methylmorpholine (2.86 g, 3.11 ml, 28.3 mmol) and 4-dimethylaminopyridine (11.5 mg, 94.2 µmol) were combined with dioxane (150 ml) to give a light brown solution. The reaction mixture was heated to 80° C. and stirred overnight. Diisopropylethyl amine (4.87 g, 6.58 ml, 37.7 mmol) was added and the mixture was cooled in an ice-bath. Iodine (4.78 g, 18.8 mmol) in dioxane (10 ml) was added and the reaction mixture was stirred overnight while warming to room temperature. The crude reaction mixture was concentrated in vacuo and purified by chromatography (silica gel-NH$_2$, 40 g, ethylacetate/heptane=50:50 to 100:0) to yield the title compound as light brown solid (1.09 g, 36%). MS: m/z=324.2 [M+H]$^+$.

Step 2

(8 endo)-3-3-Methylisothiazol-5-yl)-3-azabicyclo[3.2.1]octan-8-amine

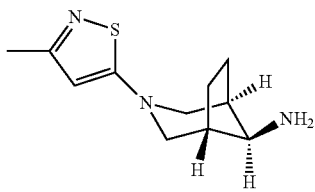

In a 250 mL round-bottomed flask, tert-butyl ((8-anti)-3-(3-methylisothiazol-5-yl)-3-azabicyclo[3.2.1]octan-8-yl)carbamate (2.99 g, 9.24 mmol) was combined with dichloromethane (180 ml) to give a brown solution. Hydrochloric acid (25%, 10 ml) was added and the reaction mixture was stirred at room temperature for 2 hours. The reaction mixture was cooled in an ice-bath, water (50 ml) was added and the mixture was basified with aqueous sodium hydroxide (4N). Extraction with dichloromethane and chromatography (silica gel-NH$_2$, 40 g, ethylacetate/heptane=50:50 to 100:0) yielded the title compound as light brown solid (1.64 g, 80%). MS: m/z=224.2 [M+H]$^+$.

Step 3, Final Coupling

N-((8 endo)-3-(3-methylisothiazol-5-yl)-3-azabicyclo[3.2.1]octan-8-yl)-5-(2,2,2-trifluoroethoxy)-[1,2,4]triazolo[1,5-a]pyridin-2-amine

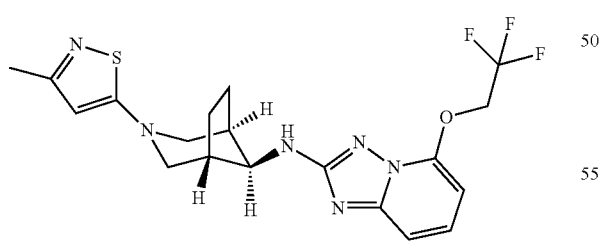

In analogy to example 1, the title compound was obtained by Buchwald coupling from 2-bromo-5-(2,2,2-trifluoroethoxy)-[1,2,4]triazolo[1,5-a]pyridine (44.4 mg, 150 µmol), intermediate 3.1 of example 1, (8-endo)-3-(3-methylisothiazol-5-yl)-3-azabicyclo[3.2.1]octan-8-amine (33.5 mg, 150 µmol) and dibromo-(tritert-butyl)-phosphine-palladium (11.7 mg, 15 µmol) as a light yellow gum (10 mg, 15.2%). HR-MS: m/z=438.14496 [M+H]$^+$.

EXAMPLE 3

8-methyl-5-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine

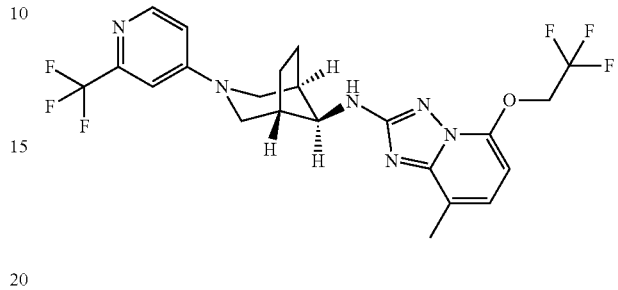

Intermediate 3.2

2-bromo-8-methyl-5-(2,2,2-trifluoroethoxy)-[1,2,4]triazolo[1,5-a]pyridine

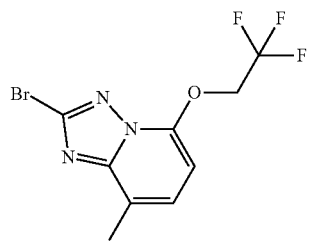 [SMILES: Cc1ccc(OCC(F)(F)F)n2nc(Br)nc12]

Step 1

3-methyl-6-(2,2,2-trifluoroethoxy)pyridin-2-amine

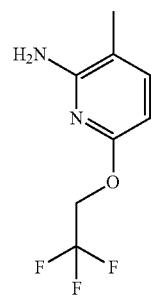

The title compound was prepared in analogy to example 1, step 1 from added 2,2,2-trifluoroethanol (1.19 g, 11.9 mmol), 6-fluoro-3-methylpyridin-2-amine (1 g, 7.93 mmol) with NaH (60%, 450 mg, 10.3 mmol) and copper (I) bromide (11.4 mg, 79.3 µmol) as a light yellow oil (1.4 g, 85.7%) HR-MS: m/z=207.07492 [M+H]$^+$.

Step 2

Ethyl N-[[3-methyl-6-(2,2,2-trifluoroethoxy)-2-pyridyl]carbamothioyl]carbamate

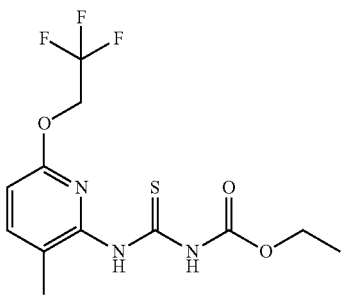 [SMILES: CCOC(=O)NC(=S)Nc1nc(OCC(F)(F)F)ccc1C]

The title compound was prepared in analogy to example 1, step 2 from 3-methyl-6-(2,2,2-trifluoroethoxy)pyridin-2-amine (0.7 g, 3.4 mmol), ethoxycarbonyl-isothiocyanate (445 mg, 3.4 mmol) as a light yellow solid (1.01 g, 88.2%. HR-MS: m/z=338.07937 [M+H]+.

Step 3

8-Methyl-5-(2,2,2-trifluoroethoxy)-[1,2,4]triazolo[1,5-a]pyridin-2-amine

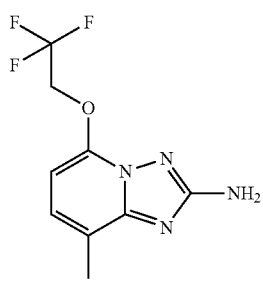 [SMILES: Cc1ccc(OCC(F)(F)F)n2nc(N)nc12]

The title compound was prepared in analogy to example 1, step 3 from Ethyl N-[[3-methyl-6-(2,2,2-trifluoroethoxy)-2-pyridyl]carbamothioyl]carbamate (1 g, 2.96 mmol), N-ethyldiisopropylamin (1.09 g, 5.88 mmol) and hydroxylamin×HCl (214 mg, 3.1 mmol) as a white solid (740 mg, 100%). HR-MS m/z=247.08058 [M+H]+.

Step 4

2-bromo-8-methyl-5-(2,2,2-trifluoroethoxy)-[1,2,4]triazolo[1,5-a]pyridine

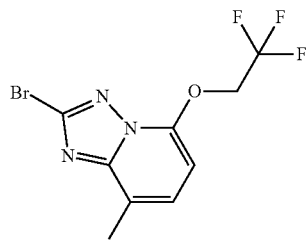 [SMILES: Cc1ccc(OCC(F)(F)F)n2nc(Br)nc12]

The title compound was prepared in analogy to example 1, step 4, from 8-methyl-5-(2,2,2-trifluoroethoxy)-[1,2,4]triazolo[1,5-a]pyridin-2-amine (740 mg, 3.01 mmol), copper (II) bromide (1.01 g, 4.51 mmol), tert-butyl nitrite (465 mg, 538 µl, 4.51 mmol) as a light yellow solid (450 mg, 48.3%). HR-MS 309.9801 (M+H)+.

Step 5, Final Coupling 8-methyl-5-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine

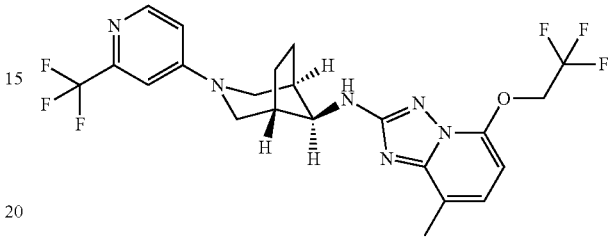

The title compound, was prepared by Buchwald coupling in analogy to example 1, from 2-bromo-8-methyl-5-(2,2,2-trifluoroethoxy)-[1,2,4]triazolo[1,5-a]pyridine (46.5 mg, 0.15 mmol) (8 endo)-3-(2-(trifluoromethyl)pyridin-4-yl)-3-azabicyclo[3.2.1]octan-8-amine, intermediate 2.1 (example 1), (40.7 mg, 0.15 mmol), with dibromobis(tri-tert-butylphosphino)dipalladium(I) in the presence of sodium tert butoxide as a white solid (31 mg, 41.3%), HR-MS ES+ (m/z): 501.18411 [(M+H)+]

EXAMPLE 4

8-methyl-N-((8 endo)-3-(6-methylpyrimidin-4-yl)-3-azabicyclo[3.2.1]octan-8-yl)-5-(2,2,2-trifluoroethoxy)-[1,2,4]triazolo[1,5-a]pyridin-2-amine

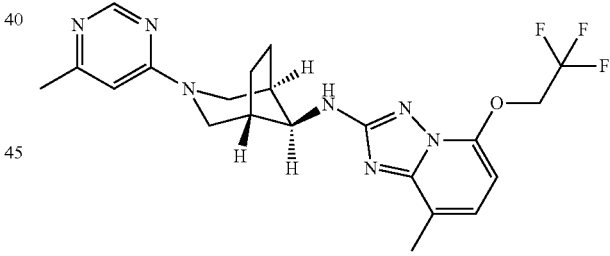

Intermediate 2.3

(8 endo)-3-6-methylpyrimidin-4-yl)-3-azabicyclo[3.2.1]octan-8-amine

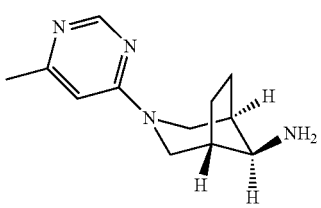 [SMILES: Cc1cc(N2C[C@H]3CC[C@@H](C2)[C@@H]3N)ncn1]

Step 1

Tert-butyl N-[(8 endo)-3-6-methylpyrimidin-4-yl)-3-azabicyclo[3.2.1]octan-8-yl]carbamate

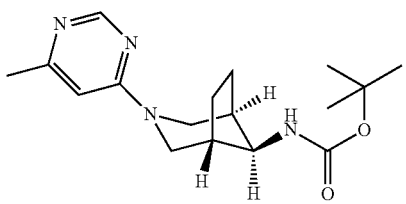 [SMILES: Cc1cc(N2C[C@H]3CC[C@@H](C2)[C@@H]3NC(=O)OC(C)(C)C)ncn1]

In a sealed tube tert-butyl (8 endo)-3-azabicyclo[3.2.1]octan-8-ylcarbamate (500 mg, 2.21 mmol) was dissolved in EtOH (10 ml) and 4-chloro-6-methylpyrimidine (869 mg, 6.63 mmol) was added followed by tri-ethylamine (894 mg, 1.23 ml, 8.84 mmol). The reaction mixture was stirred in the sealed tube at 130° C. overnight. The crude reaction mixture was concentrated in vacuum. The residue was diluted with 20 mL of dichloromethane and 20 mL of water. The organic phase were extracted with DCM (3×20 mL), dried over MgSO$_4$ and concentrated in vacuum. The crude material was purified by flash chromatography (0% to 100% EtOAc in heptane) to afford the title compound as a yellow solid (496 mg, 71% yield).

MS ES+ (m/z): 319.2 [(M+H)$^+$]

Step 2

(8 endo)-3-(6-methylpyrimidin-4-yl)-3-azabicyclo[3.2.1]octan-8-amine

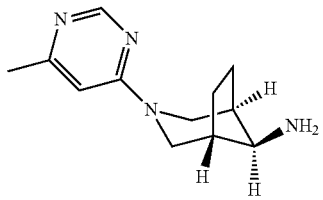 [SMILES: Cc1cc(N2C[C@H]3CC[C@@H](C2)[C@@H]3N)ncn1]

To a light yellow solution of tert-butyl N-[(8 endo)-3-(6-methylpyrimidin-4-yl)-3-azabicyclo[3.2.1]octan-8-yl]carbamate_(260 mg, 817 µmol) in dichloromethane (8 ml) was added TFA (931 mg, 629 µl, 8.17 mmol). The reaction mixture was stirred at room temperature overnight and concentrated in vacuum. The crude material was purified by Ion-exchange column (Si-SCX-2, 10 g, washed with MeOH and liberated with MeOH (NH$_3$ M)) to afford the title compound (195 mg, 804 µmol, 98.5% yield) that was used in the next step without further purification. MS ES+ (m/z): 219.2 [(M+H)$^+$]

Step 3, Final Coupling 8-methyl-N-((8 endo)-3-(6-methylpyrimidin-4-yl)-3-azabicyclo[3.2.1]octan-8-yl)-5-(2,2,2-trifluoroethoxy)-[1,2,4]triazolo[1,5-a]pyridin-2-amine

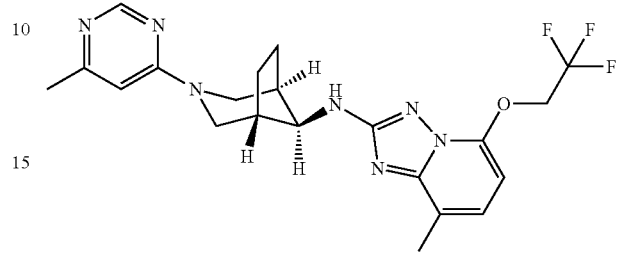

The title compound, was prepared by Buchwald coupling in analogy to example 1, from 2-bromo-8-methyl-5-(2,2,2-trifluoroethoxy)-[1,2,4]triazolo[1,5-a]pyridine (intermediate 3.2 example 3) (46.5 mg, 0.15 mmol), ((8 endo)-3-(6-methylpyrimidin-4-yl)-3-azabicyclo[3.2.1]octan-8-amine (32.7 mg, 0.15 mmol) with dibromobis(tri-tert-butylphosphino) dipalladium(I) in the presence of sodium tert-butoxide as a light yellow foam (31 mg, 41.3%), HR-MS ES–(m/z): 446.19194 [(M–H)$^-$]

EXAMPLE 5

N-((8 endo)-3-(2-chloropyridin-4-yl)-3-azabicyclo[3.2.1]octan-8-yl)-8-methyl-5-(2,2,2-trifluoroethoxy)-[1,2,4]triazolo pyridin-2-amine

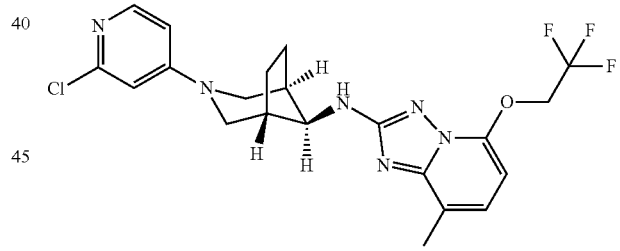

Intermediate 2.4

(8 endo)-3-2-chloropyridin-4-yl)-3-azabicyclo[3.2.1]octan-8-amine

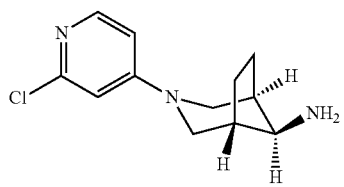 [SMILES: N[C@@H]1[C@@H]2CC[C@H]1CN(c1ccnc(Cl)c1)C2]

Step 1

Tert-butyl N-[(8 endo)-3-2-chloropyridin-4-yl)-3-azabicyclo[3.2.1]octan-8-yl]carbamate

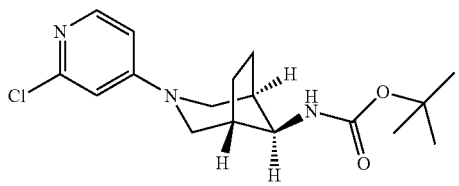 [SMILES: CC(C)(C)OC(=O)N[C@@H]1[C@@H]2CC[C@H]1CN(c1ccnc(Cl)c1)C2]

The title compound was made in analogy to intermediate 2.1 step 1, (example 1) from tert-butyl (8 endo)-3-azabicyclo[3.2.1]octan-8-ylcarbamate (120 mg, 530 µmol) in NMP (2 ml), DIPEA (137 mg, 185 µl, 1.06 mmol) and 2-chloro-4-fluoropyridine (76.7 mg, 583 µmol1) as a white powder. 146.9 mg, 82%. MS ES+ (m/z)=338.2 [(M+H)+]

Step 2

(8 endo)-3-2-chloropyridin-4-yl)-3-azabicyclo[3.2.1]octan-8-amine

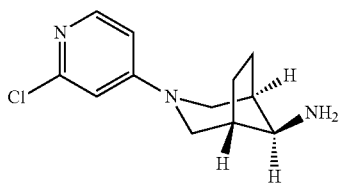 [SMILES: N[C@@H]1[C@@H]2CC[C@H]1CN(c1ccnc(Cl)c1)C2]

The compound was prepared in analogy to intermediate 2.1 (step 2, example 1) from tert-butyl N [(8 endo)-3-(2-chloropyridin-4-yl)-3-azabicyclo[3.2.1]octan-8-yl]carbamate (146.9 mg, 435 µmol) in dichloromethane in the presence of HCl 37% (257 mg, 214 µl, 2.61 mmol). The title compound was obtained as a white solid (89.9 mg, 378 µmol, 87% yield) MS ES+ (m/z): 238.1 [(M+H)+]

Step 3, Final Coupling

N-((8 endo)-3-(2-chloropyridin-4-yl)-3-azabicyclo[3.2.1]octan-8-yl)-8-methyl-5-(2,2,2-trifluoroethoxy)-[1,2,4]triazolo[1,5-a]pyridin-2-amine

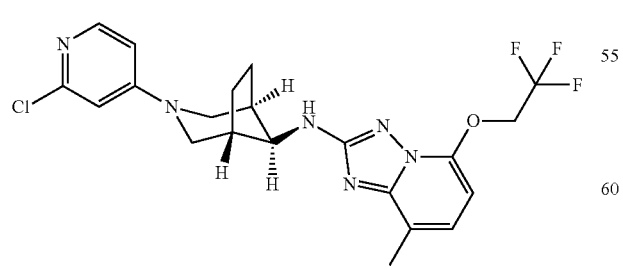

The title compound, was prepared by Buchwald coupling in analogy to example 1, from 2-bromo-8-methyl-5-(2,2,2-trifluoroethoxy)-[1,2,4]triazolo[1,5-a]pyridine (intermediate 3.2 example 3) (46.5 mg, 0.15 mmol) (8 endo)-3-(2-chloropyridin-4-yl)-3-azabicyclo[3.2.1]octan-8-amine (35.7 mg, 0.15 mmol) with dibromobis(tri-tert-butylphosphino)dipalladium(I) in the presence of sodium tert-butoxide as a light yellow foam (32 mg, 45.7%), HR-MS ES+ (m/z): 467.15777 [(M+H)+]

EXAMPLE 6

N-((8 endo)-3-(2-methoxypyridin-4-yl)-3-azabicyclo[3.2.1]octan-8-yl)-8-methyl-5-(2,2,2-trifluoroethoxy)-[1,2,4]triazolo[1,5-a]pyridin-2-amine

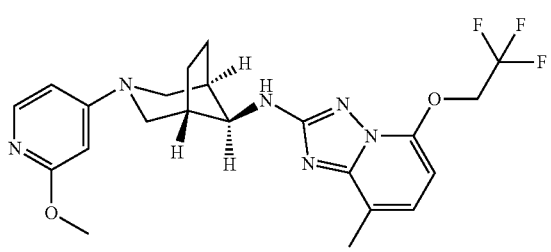 [SMILES: COc1cc(N2C[C@H]3CC[C@@H](C2)[C@@H]3Nc2nc3c(C)ccc(OCC(F)(F)F)n3n2)ccn1]

Intermediate 2.5

(8-endo)-3-(2-methoxy-4-pyridyl)-3-azabicyclo[3.2.1]octan-8-amine

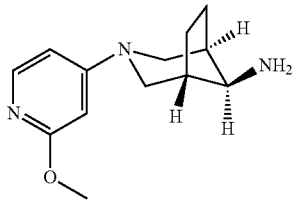 [SMILES: COc1cc(N2C[C@H]3CC[C@@H](C2)[C@@H]3N)ccn1]

Step 1 tert-butyl N-[(8-endo)-3-(2-methoxy-4-pyridyl)-3-azabicyclo[3.2.1]octan-8-yl]carbamate

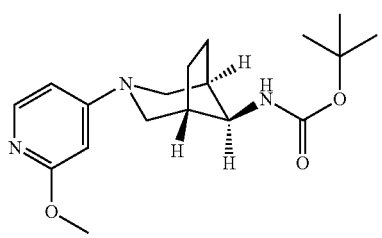 [SMILES: COc1cc(N2C[C@H]3CC[C@@H](C2)[C@@H]3NC(=O)OC(C)(C)C)ccn1]

The title compound was made in analogy to intermediate 2.1 step 1, (example 1) from tert-butyl (8 endo)-3-azabicyclo[3.2.1]octan-8-ylcarbamate (890 mg, 3.93 mmol) in NMP (1.43 ml), DIPEA (1.02 g, 7.87 mmol) and 4-fluoro-2-methoxypyridine (0.5 g, 436 µl, 3.93 mmol) as a white foam, 480 mg, 36.6%. MS ES+ (m/z): 334.2 [(M+H)+].

Step 2

8-endo)-3-2-methoxy-4-pyridyl)-3-azabicyclo[3.2.1]octan-8-amine

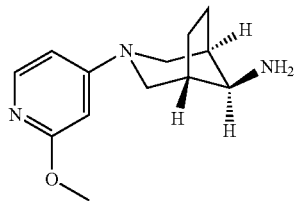 [SMILES: COc1cc(N2C[C@H]3CC[C@@H](C2)[C@@H]3N)ccn1]

The title compound was prepared in analogy to intermediate 2.1 (step 2, example 1) using tert-butyl ((8-endo)-3-(2-methoxypyridin-4-yl)-3-azabicyclo[3.2.1]octan-8-yl)carbamate (480 mg, 1.44 mmol) in dichloromethane in the presence of TFA (821 mg, 7.2 mmol). The title compound was obtained as a white solid (336 mg, 70% yield) MS ES+ (m/z): 234.2 [(M+H)+]

Step 3, Final Coupling

N-((8 endo)-3-(2-methoxypyridin-4-yl)-3-azabicyclo[3.2.1]octan-8-yl)-8-methyl-5-(2,2,2-trifluoroethoxy)-[1,2,4]triazolo[1,5-a]pyridin-2-amine

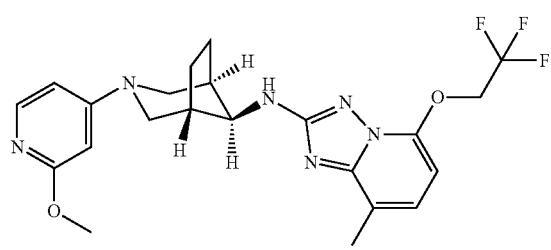 [SMILES: COc1cc(N2C[C@H]3CC[C@@H](C2)[C@@H]3Nc2nc3c(C)ccc(OCC(F)(F)F)n3n2)ccn1]

The title compound, was prepared by Buchwald coupling in analogy to example 1, from 2-bromo-8-methyl-5-(2,2,2-trifluoroethoxy)-[1,2,4]triazolo[1,5-a]pyridine (intermediate 3.2 example 3) (30 mg, 96.8 µmol), 8-endo)-3-(2-methoxy-4-pyridyl)-3-azabicyclo[3.2.1]octan-8-amine (22.6 mg, 96.8 µmol) with dibromobis(tri-tert-butylphosphino)dipalladium (I) in the presence of sodium tert butoxide as a white foam (27.6 mg, 61.7%), HR-MS ES+ (m/z): 463.2069 [(M+H)+]

EXAMPLE 7

N-((8 endo)-3-(6-chloropyridazin-4-yl)-3-azabicyclo[3.2.1]octan-8-yl)-8-methyl-5-(2,2,2-trifluoroethoxy)-[1,2,4]triazolo[1,5-a]pyridin-2-amine

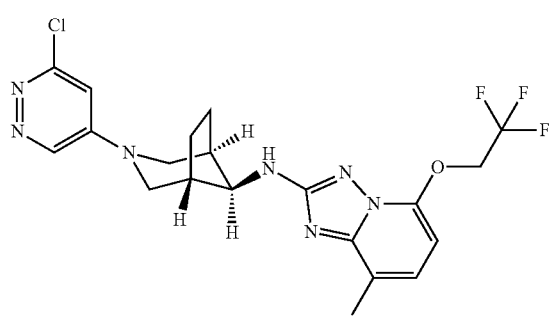 [SMILES: Cc1ccc(OCC(F)(F)F)n2nc(N[C@@H]3[C@@H]4CC[C@H]3CN(c3cnnc(Cl)c3)C4)nc12]

Intermediate 2.6

(8-endo)-3-(6-chloropyridazin-4-yl)-3-azabicyclo[3.2.1]octan-8-amine

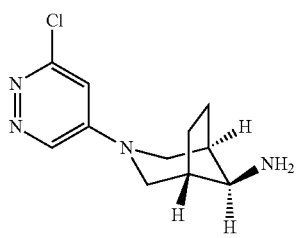 [SMILES: N[C@@H]1[C@@H]2CC[C@H]1CN(c1cnnc(Cl)c1)C2]

Step 1 tert-Butyl N-[(8-endo)-3-(6-chloropyridazin-4-yl)-3-azabicyclo[3.2.1]octan-8-yl]carbamate

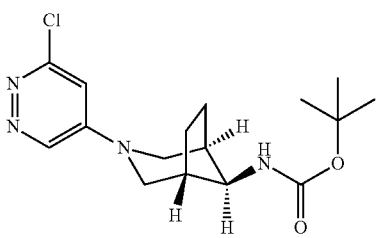 [SMILES: CC(C)(C)OC(=O)N[C@@H]1[C@@H]2CC[C@H]1CN(c1cnnc(Cl)c1)C2]

The title compound was made in analogy to intermediate 2.1 step 1, (example 1) from tert-butyl (8 endo)-3-azabicyclo[3.2.1]octan-8-ylcarbamate (700 mg, 3.09 mmol), 3,5-dichloropyridazine (691 mg, 4.64 mmol) in ethanol (42 ml), with triethylamine (1.25 g, 12.4 mmol) and stirring for 3 h at 85° C. and then 60 h at RT, as a yellow solid, 923 mg, 88%. MS ES+ (m/z): 339.2 [(M+H)+].

Step 2

(8-endo)-3-(6-chloropyridazin-4-yl)-3-azabicyclo[3.2.1]octan-8-amine

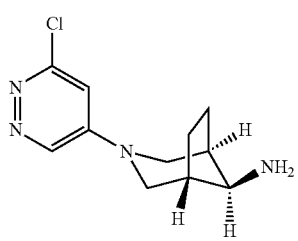 [SMILES: N[C@@H]1[C@@H]2CC[C@H]1CN(c1cnnc(Cl)c1)C2]

The compound was prepared in analogy to intermediate 2.1 (step 2, example 1) from tert-butyl N-[(8-endo)-3-(6-chloropyridazin-4-yl)-3-azabicyclo[3.2.1]octan-8-yl]carbamate (923 mg, 2.72 mmol) in dichloromethane in the presence of HCl 37% (1.61 g 16.3 mmol). The title compound was obtained as a brown solid (651 mg, 100% yield) MS ES+ (m/z): 239.1 [(M+H)+]

Step 3, Final Coupling

N-((8 endo)-3-(6-chloropyridazin-4-yl)-3-azabicyclo[3.2.1]octan-8-yl)-8-methyl-5-(2,2,2-trifluoroethoxy)-[1,2,4]triazolo[1,5-a]pyridin-2-amine

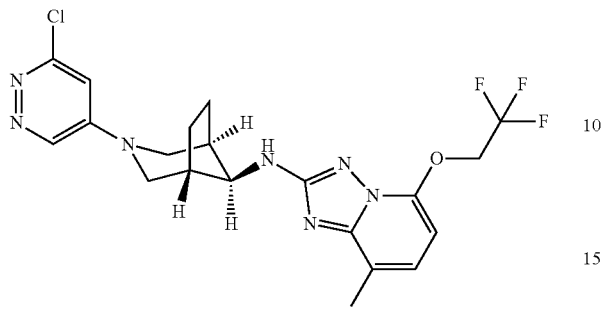

The title compound, was prepared by Buchwald coupling in analogy to example 1, from 2-bromo-8-methyl-5-(2,2,2-trifluoroethoxy)-[1,2,4]triazolo[1,5-a]pyridine (intermediate 3.2 example 3) (28 mg, 90.3 µmol), ((8-endo)-3-(6-chloro-pyridazin-4-yl)-3-azabicyclo[3.2.1]octan-8-amine (21.6 mg, 90.3 µmol) with Pd$_2$(dba)3.CHCl$_3$ (8.39 mg, 8.11 µmol) in the presence of sodium tert-butoxide and Q-Phos in a microwave at 120° C. during 20 min. It was obtained as a white solid (15.5 mg, 36.7% yield). HR-MS ES+ (m/z): 468.1533 [(M+H)$^+$].

EXAMPLE 8

2-(5-(2,2,2-trifluoroethoxy)-2-(((8 endo)-3-(2-(trifluoromethyl)pyridin-4-yl)-3-azabicyclo[3.2.1]octan-8-yl)amino)-[1,2,4]triazolo[1,5-a]pyridin-8-yl)propan-2-ol

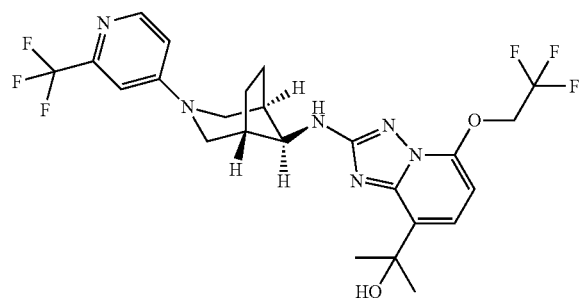

Intermediate 3.3

2-[2-bromo-5-(2,2,2-trifluoroethoxy)-[1,2,4]triazolo[1,5-a]pyridin-8-yl]propan-2-ol

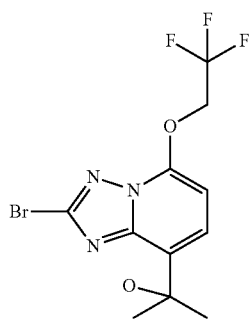 [SMILES: CC(C)(O)c1ccc(OCC(F)(F)F)n2nc(Br)nc12]

Step 1

Methyl-2-amino-6-(2,2,2-trifluoroethoxy)pyridine-3-carboxylate

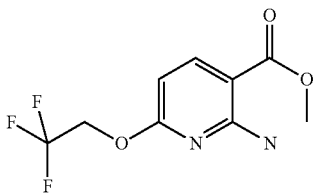

To a stirred solution of methyl 2-amino-6-chloropyridine-3-carboxylate (5.0 g, 26.89 mmol) in DMF (40 ml) was added potassium tert-butoxide (4.5 g, 40.3 mmol), 2,2,2-trifluoro-ethanol (5.4 g, 53.8 mmol) followed by the addition of copper (I) bromide (0.36 g, 2.7 mmol) under argon atmosphere. The reaction mixture was heated to 120° C. for 48 hours. TLC and LC-MS showed the reaction was complete. The reaction mixture was partitioned between water (100 ml) and EtOAc (100 ml), the organic layer was separated, the aqueous layer were extracted with EtOAc (2×50 ml). The combined organic layers were washed with brine (50 ml, 3 times) and it was dried over Na$_2$SO$_4$ and concentrated under vacuum to provide the crude material. It was purified by flash chromatography using 0-10% EtOAc in hexane to afford methyl 2-amino-6-(2,2,2-trifluoroethoxy) pyridine-3-carboxylate (0.8 g, 12%) as off white semisolid. MS ES+ (m/z): 251.1 [(M+H)+].

Step 2

2-[2-amino-6-(2,2,2-trifluoroethoxy) pyridin-3-yl]propan-2-ol

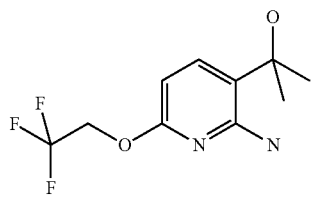 [SMILES: CC(C)(O)c1ccc(OCC(F)(F)F)nc1N]

To a stirred solution of methyl 2-amino-6-(2,2,2-trifluoroethoxy) pyridine-3-carboxylate (1.6 g, 6.4 mmol) in THF (40.0 ml) was added methyl magnesium bromide (20 ml) at −25° C. and stirred at 25° C. for 18 h. TLC monitoring indicated formation of desired product along with other impurities. Reaction mass was quenched by ice water (50 ml), aqueous layer were extracted by ethyl acetate (3×50 ml). The combined organic layers were washed with brine (50 ml) and it was dried over Na$_2$SO$_4$ and concentrated under vacuum to provide crude residue. It was purified using flash chromatography, 0-100% EtOAc in hexane, to afford 2-[2-amino-6-(2,2,2-trifluoroethoxy) pyridin-3-yl]propan-2-ol (1.2 g. 75%) as brown semisolid. MS ES+ (m/z): 251.1 [(M+H)+].

Step 3

Ethyl N-{[3-(2-hydroxypropan-2-yl)-6-(2,2,2-trifluoroethoxy)pyridin-2-yl]carbamothioyl}carbamate

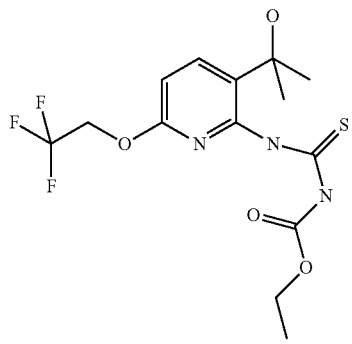 [SMILES: CCOC(=O)NC(=S)Nc1nc(OCC(F)(F)F)ccc1C(C)(C)O]

To a stirred solution of 2-[2-amino-6-(2,2,2-trifluoroethoxy) pyridin-3-yl]propan-2-ol (650 mg, 2.6 mmol) in dioxane (14 ml) was added ethoxycarbonylisothiocyanate (734 mg, 6.5 mmol) diluted with dioxane (1 ml) into the reaction mass and stirred at 25° C. for 18 h. TLC/Crude LCMS monitoring indicated formation of desired product. It was evaporated in vacuo to provide crude compound. Crude was washed with hexane (2×10 ml) followed by dried in vacuo to provide crude ethyl N-{[3-(2-hydroxypropan-2-yl)-6-(2,2,2-trifluoro ethoxy)pyridin-2-yl]carbamothioyl}carbamate (750 mg) as light yellow semisolid. It was used in next step for further reaction without purification. MS ES+ (m/z): 381.6 [(M+H)$^+$].

Step 4

2-[2-amino-5-(2,2,2-trifluoroethoxy)-[1,2,4]triazolo[1,5-a]pyridin-8-yl]propan-2-ol

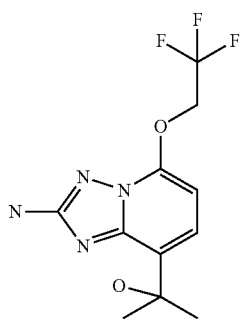 [SMILES: CC(C)(O)c1ccc(OCC(F)(F)F)n2nc(N)nc12]

To a stirred solution of ethyl N-{[3-(2-hydroxypropan-2-yl)-6-(2,2,2-trifluoroethoxy)pyridin-2-yl]carbamothioyl}carbamate (1.1 g, 2.89 mmol) in ethanol (20 ml) were added hydroxyl amine hydrochloride (500 mg, 7.2 mmol) and DIPEA (2.0 ml, 11.6 mmol) into the reaction mass and reflux at 80° C. for 4 h. The reaction mass was concentrated under vacuum to provide crude product which was purified by flash column chromatography using 0-50% EtOAc in hexane to provide 2-[2-amino-5-(2,2,2-trifluoroethoxy)-[1,2,4]triazolo[1,5-a]pyridin-8-yl]propan-2-ol (570 mg, 52%, two step yield) as off white solid. MS ES+ (m/z): 290.8 [(M+H)$^+$].

Step 5

2-[2-bromo-5-(2,2,2-trifluoroethoxy)-[1,2,4]triazolo[1,5-a]pyridin-8-yl]propan-2-ol

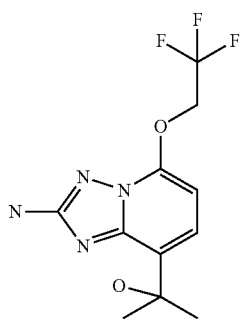 [SMILES: CC(C)(O)c1ccc(OCC(F)(F)F)n2nc(N)nc12]

To a stirred solution of 2-[2-amino-5-(2,2,2-trifluoroethoxy)-[1,2,4]triazolo[1,5-a]pyridin-8-yl]propan-2-ol (450 mg, 1.55 mmol) in 47% HBr (2.5 ml) was added sodium nitrite (215 mg, 3.10 mmol) into the reaction mass at 0° C. for 10 min. Reaction mass was stirred for 20 min after that CuBr2 (522 mg, 2.33 mmol) was added and stirred for 17 h at 25° C. To the crude mass water (25 ml) was added and reaction mass was neutralized by 10% NaHCO$_3$ (25 ml) and the aqueous layer was extracted with EtOAc (3 times 25 ml). The combined organic layers were washed 5% ammonium hydroxide solution (3×20 ml). It was dried over Na$_2$SO$_4$ followed by concentration under vacuum to provide crude residue which was purified by flash column chromatography to afford 2-[2-bromo-5-(2,2,2-triflouroethoxy)-[1,2,4]triazolo[1,5-a]pyridine-8-yl]propan-2-ol (275 mg, 50%) as off white solid. MS ES+ (m/z): 355.7 [(M+H)$^+$].

Step 6, Final Coupling

2-(5-(2,2,2-trifluoroethoxy)-2-(((8 endo)-3-(2-(trifluoromethyl)pyridin-4-yl)-3-azabicyclo[3.2.1]octan-8-yl)amino)-[1,2,4]triazolo[1,5-a]pyridin-8-yl)propan-2-ol

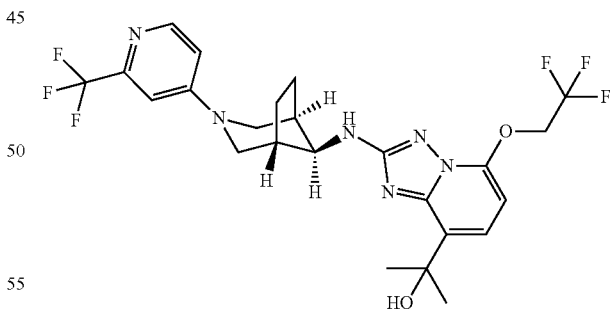

The title compound, was prepared by Buchwald coupling in analogy to example 1, from 2-[2-bromo-5-(2,2,2-trifluoroethoxy)-[1,2,4]triazolo[1,5-a]pyridin-8-yl]propan-2-ol (35 mg, 98.8 μmol), (8-endo)-3-(2-(trifluoromethyl)pyridin-4-yl)-3-azabicyclo[3.2.1]octan-8-amine (26.8 mg, 9.88 μmol) with Pd$_2$(dba)$_3$·CHCl$_3$ (9.05 mg, 9.88 μmol) in the presence of sodium tert-butoxide and Xanthphos in a microwave at 120° C. during 20 min. It was obtained as a white solid (7.6 mg, 14.1% yield). HR-MS ES+ (m/z): 545.2104 [(M+H)+].

EXAMPLE 9

2-(2-(((8 endo)-3-(6-methylpyrimidin-4-yl)-3-azabicyclo[3.2.1]octan-8-yl)amino)-5-(2,2,2-trifluoroethoxy)-[1,2,4]triazolo[1,5-a]pyridin-8-yl)propan-2-ol

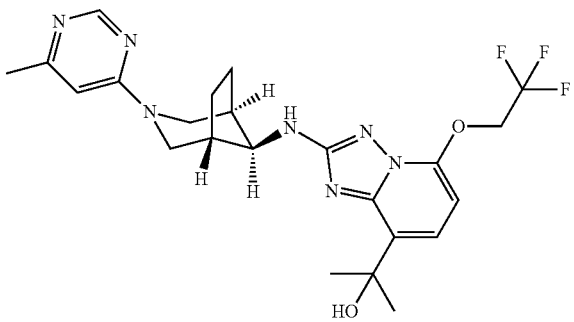 [SMILES: Cc1cc(N2C[C@H]3CC[C@@H](C2)[C@@H]3Nc2nc3c(C(C)(C)O)ccc(OCC(F)(F)F)n3n2)ncn1]

The title compound, was prepared by Buchwald coupling in analogy to example 1, from 2-[2-bromo-5-(2,2,2-trifluoroethoxy)-[1,2,4]triazolo[1,5-a]pyridin-8-yl]propan-2-ol (40 mg, 113 μmol), intermediate 3.3 example 8, (8-endo)-3-(6-methylpyrimidin-4-yl)-3-azabicyclo[3.2.1]octan-8-amine (24.7 mg, 113 μmol), intermediate 2.3 example 4, with Pd$_2$(dba)$_3$·CHCl$_3$ (10.3 mg, 11.3 μmol) in the presence of sodium tert-butoxide and Xanthphos in a microwave at 120° C. during 20 min. It was obtained as a light yellow gum (8 mg, 14.4% yield). HR-MS ES+ (m/z): 492.2338 [(M+H)+].

EXAMPLE 10

2-(2-((3-(difluoromethoxy)-4-(3-methyl-1H-1,2,4-triazol-1-yl)phenyl)amino)-5-(2,2,2-trifluoroethoxy)-[1,2,4]triazolo pyridin-8-yl)propan-2-ol

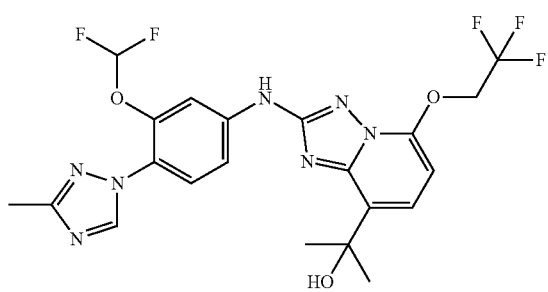 [SMILES: Cc1ncn(-c2ccc(Nc3nc4c(C(C)(C)O)ccc(OCC(F)(F)F)n4n3)cc2OC(F)F)n1]

Intermediate 2.7

3-(difluoromethoxy)-4-(3-methyl-1,2,4-triazol-1-yl)aniline

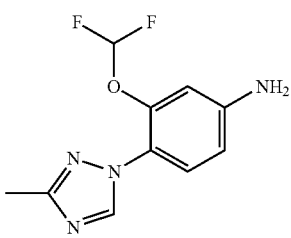 [SMILES: Cc1ncn(-c2ccc(N)cc2OC(F)F)n1]

The title compound was prepared as described by K. M. Boy et al in WO2015/153709 A1.

Coupling Step 2-(2-((3-difluoromethoxy)-4-(3-methyl-1H-1,2,4-triazol-1-yl)phenyl)amino)-5-(2,2,2-trifluoroethoxy)-[1,2,4]triazolo[1,5-a]pyridin-8-yl)propan-2-ol

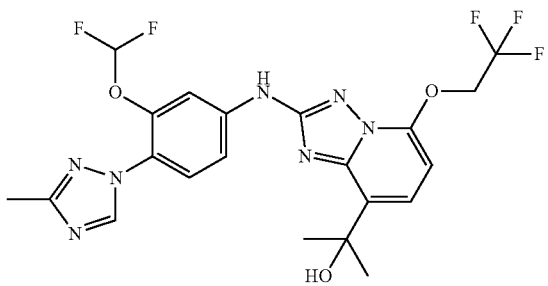 [SMILES: Cc1ncn(-c2ccc(Nc3nc4c(C(C)(C)O)ccc(OCC(F)(F)F)n4n3)cc2OC(F)F)n1]

The title compound, was prepared by Buchwald coupling in analogy to example 1, from 2-[2-bromo-5-(2,2,2-trifluoroethoxy)-[1,2,4]triazolo[1,5-a]pyridin-8-yl]propan-2-ol (40 mg, 113 μmol), intermediate 3.3, example 8, and 3-(difluoromethoxy)-4-(3-methyl-1H-1,2,4-triazol-1-yl)aniline (27.1 mg, 113 μmol) with Pd$_2$(dba)$_3$·CHCl$_3$ (10.3 mg, 113 μmol) in the presence of sodium tert-butoxide and Xanthphos in a microwave at 120° C. during 20 min. It was obtained as off white solid (12 mg, 20.7% yield). HR-MS ES+ (m/z): 514.21641 [(M+H)+].

EXAMPLE 11

8-isopropyl-5-(2,2,2-trifluoroethoxy)-N-((8 endo)-3-(2-(trifluoromethyl)pyridin-4-yl)-3-azabicyclo[3.2.1]octan-8-yl)-[1,2,4]triazolo[1,5-a]pyridin-2-amine

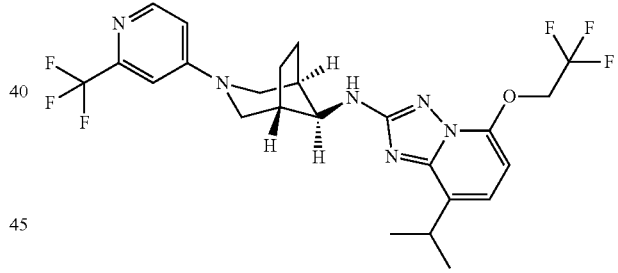

Intermediate 3.4

2-bromo-8-isopropyl-5-(2,2,2-trifluoroethoxy)-[1,2,4]triazolo[1,5-a]pyridine

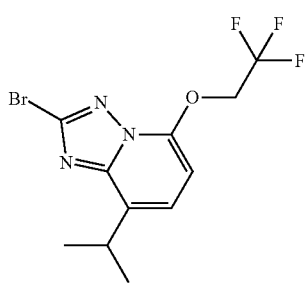 [SMILES: CC(C)c1ccc(OCC(F)(F)F)n2nc(Br)nc12]

Step 1

2-bromo-8-isopropyl-5-(2,2,2-trifluoroethoxy)-[1,2,4]triazolo[1,5-a]pyridine

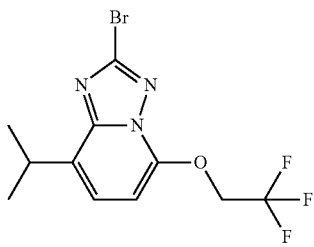 [SMILES: CC(C)c1ccc(OCC(F)(F)F)n2nc(Br)nc12]

To a stirred solution of 2-[2-bromo-5-(2,2,2-trifluoroethoxy)-[1,2,4]triazolo[1,5-a]pyridin-8-yl]propan-2-ol (0.65 g), intermediate 3.3 of example 8, in TFA (2.0 ml) was added triethylsilane (1.1 ml, 7.0 mmol) into the reaction mass at 0° C. The reaction mass was stirred for 24 h at 25° C. until TLC/Crude LCMS monitoring indicated completion of reaction. The mixture was evaporated in vacuo to provide the crude residue. To the crude residue water (20 ml) was added, the crude mass was neutralized by 10% NaHCO₃ (20 ml) and extracted with EtOAc (3 times 50 ml). The combined organic layers were washed with brine (50 ml), s dried over Na₂SO₄ filtered and the solvent was evaporated in vacuo to provide crude product which was purified by flash column chromatography to afford the title compound (0.36 g, 49%) as off white solid. HR-MS ES+ (m/z): 339.7 [(M+H)+].

Step 2, Coupling Step 8-isopropyl-5-(2,2,2-trifluoroethoxy)-N-((8 endo)-3-2-(trifluoromethyl)pyridin-4-yl)-3-azabicyclo[3.2.1]octan-8-yl)-[1,2,4]triazolo[1,5-a]pyridin-2-amine

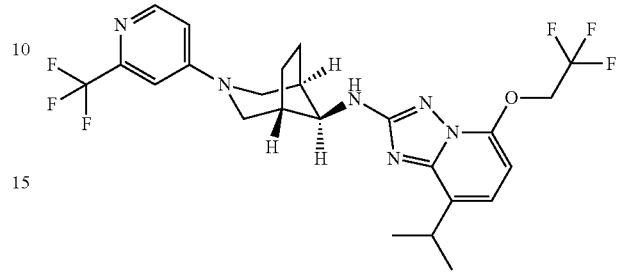

The title compound, was prepared by Buchwald coupling in analogy to example 1, from 2-bromo-8-isopropyl-5-(2,2,2-trifluoroethoxy)-[1,2,4]triazolo[1,5-a]pyridine (30 mg, 88.7 μmol) ((8-endo)-8-methyl-3-(2-(trifluoromethyl)pyridin-4-yl)-3-azabicyclo[3.2.1]octan-8-amine (25.3 mg, 88.7 μmol), intermediate 2.1, example 1, with Pd₂(dba)₃. CHCl₃ (8.12 mg, 8.87 μmol) in the presence of sodium tert-butoxide and Xanthphos in a microwave at 120° C. during 20 min. It was obtained as an off-light foam (12.4 mg, 26.4% yield). HR-MS ES+ (m/z): 529.2168 [(M+H)+].

EXAMPLES 12-21

According to the coupling procedure described in example 11 step 2, further derivatives have been prepared by Buchwald coupling from the respective intermediate 3.4 and intermediates 2 as comprised in the table below and described below:

| Examples number | Systematic name Yield of reaction | Starting materials | MW found (M + H)+ |
|---|---|---|---|
| 12 | 8-isopropyl-N-((8 endo)-3-(6-methylpyrimidin-4-yl)-3-azabicyclo[3.2.1]octan-8-yl)-5-(2,2,2-trifluoroethoxy)-[1,2,4]triazolo[1,5-a]pyridin-2-amine (42 mg, 16.9%) | 2-bromo-8-isopropyl-5-(2,2,2-trifluoroethoxy)-[1,2,4]triazolo[1,5-a]pyridine (intermediate 3.4) (30 mg, 88.7 μmol) and (8 endo)-3-(6-methylpyrimidin-4-yl)-3-azabicyclo[3.2.1]octan-8-amine, (19.4 mg, 88.7 μmol), intermediate 2.3, example 4. | 476.2399 (HR) |
| 13 | N-((8 endo)-3-(2-chloropyridin-4-yl)-3-azabicyclo[3.2.1]octan-8-yl)-8-isopropyl-5-(2,2,2-trifluoroethoxy)-[1,2,4]triazolo[1,5-a]pyridin-2-amine (22 mg, 50.1%) | 2-bromo-8-isopropyl-5-(2,2,2-trifluoroethoxy)-[1,2,4]triazolo[1,5-a]pyridine (intermediate 3.4) (30 mg, 88.7 μmol) and ((8 endo)-3-(2-chloropyridin-4-yl)-3-azabicyclo[3.2.1]octan-8-amine, (21.1 mg, 88.7 μmol), intermediate 2.4, example 5. | 495.1891 (HR) |

| Examples number | Systematic name<br>Yield of reaction | Starting materials | MW found (M + H)⁺ |
|---|---|---|---|
| 14 | 8-Isopropyl-N-((8 endo)-3-(2-methoxypyridin-4-yl)-3-azabicyclo[3.2.1]octan-8-yl)-5-(2,2,2-trifluoroethoxy)-[1,2,4]triazolo[1,5-a]pyridin-2-amine (10 mg, 17.2%) | 2-bromo-8-isopropyl-5-(2,2,2-trifluoroethoxy)-[1,2,4]triazolo[1,5-a]pyridine (intermediate 3.4) (40 mg, 118 μmol) and (8-endo)-3-(2-methoxypyridin-4-yl)-3-azabicyclo[3.2.1]octan-8-amine (27.6 mg, 118 μmol), intermediate 2.5, example 6. | 491.3 |
| 15 | N-((8 endo)-3-(6-chloropyridazin-4-yl)-3-azabicyclo[3.2.1]octan-8-yl)-8-isopropyl-5-(2,2,2-trifluoroethoxy)-[1,2,4]triazolo[1,5-a]pyridin-2-amine | 2-bromo-8-isopropyl-5-(2,2,2-trifluoroethoxy)-[1,2,4]triazolo[1,5-a]pyridine (intermediate 3.4) (33.8 mg, 100 μmol) and (8-endo)-3-(6-chloropyridazin-4-yl)-3-azabicyclo[3.2.1]octan-8-amine (23 mg, 100 μmol) intermediate 2.6, example 7 | 496.1849 (HR) |
| 16 | N-(3-(difluoromethoxy)-4-(3-methyl-1H-1,2,4-triazol-1-yl)phenyl)-8-isopropyl-5-(2,2,2-trifluoroethoxy)-[1,2,4]triazolo[1,5-a]pyridin-2-amine (18.8 mg, 42.6%) | 2-bromo-8-isopropyl-5-(2,2,2-trifluoroethoxy)-[1,2,4]triazolo[1,5-a]pyridine (intermediate 3.4) (30 mg, 88.7 μmol) and 3-(difluoromethoxy)-4-(3-methyl-1,2,4-triazol-1-yl)aniline (21.3 mg, 88.7 μmol), intermediate 2.7, example 10. | 498.1699 (HR) |
| 17 | 8-isopropyl-N-((8 endo)-3-(6-methoxypyridazin-4-yl)-3-azabicyclo[3.2.1]octan-8-yl)-5-(2,2,2-trifluoroethoxy)-[1,2,4]triazolo[1,5-a]pyridin-2-amine (22 mg, 44.8%) | 2-bromo-8-isopropyl-5-(2,2,2-trifluoroethoxy)-[1,2,4]triazolo[1,5-a]pyridine (intermediate 3.4) (33.8 mg, 100 μmol) and (8 endo)-3-(6-methoxypyridazin-4-yl)-3-azabicyclo[3.2.1]octan-8-amine (23.4 mg, 100 μmol), intermediate 2.8, below. | 492.2347 (HR) |

-continued

| Examples number | Systematic name<br>Yield of reaction | Starting materials | MW found (M + H)+ |
|---|---|---|---|
| 18 | 8-Isopropyl-N-((8 endo)-3-(3-methyl-1,2,4-oxadiazol-5-yl)-3-azabicyclo[3.2.1]octan-8-yl)-5-(2,2,2-trifluoroethoxy)-[1,2,4]triazolo[1,5-a]pyridin-2-amine (12.7 mg, 46.1%) | 2-bromo-8-(propan-2-yl)-5-(2,2,2-trifluoroethoxy)-[1,2,4]triazolo[1,5-a]pyridine (intermediate 3.4) (20 mg, 59.1 µmol) and 8-endo-3-(3-methyl-1,2,4-oxadiazol-5-yl)-3-azabicyclo[3.2.1]octan-8-amine (12.3 mg, 59.1 µmol), intermediate 2.9, below | 466.2189 (HR) |
| 19 | 8-Isopropyl-N-(3-methoxy-4-(3-methyl-1H-1,2,4-triazol-1-yl)phenyl)-5-(2,2,2-trifluoroethoxy)-[1,2,4]triazolo[1,5-a]pyridin-2-amine (30 mg, 48.9%) | 2-bromo-8-(propan-2-yl)-5-(2,2,2-trifluoroethoxy)-[1,2,4]triazolo[1,5-a]pyridine (intermediate 3.4) (45 mg, 133 µmol) and 3-methoxy-4-(3-methyl-1,2,4-triazol-1-yl)aniline, (27.2 mg, 133 µmol), intermediate 2.01, below. | 462.1882 |
| 20 | 5-((8-isopropyl-5-(2,2,2-trifluoroethoxy)-[1,2,4]triazolo[1,5-a]pyridin-2-yl)amino)-2-(4-methyl-1H-imidazol-1-yl)benzonitrile (2.9 mg, 6.37%) | 2-bromo-8-(propan-2-yl)-5-(2,2,2-trifluoroethoxy)-[1,2,4]triazolo[1,5-a]pyridine (intemediate 3.4) (33.8 mg, 100 µmol) and 5-amino-2-(4-methylimidazol-1-yl)benzonitrile (19.8 mg, 100 µmol), (intermediate 2.02, below. | 456.1761 (HR) |
| 21 | 8-isopropyl-N-(3-methoxy-4-(2-methylpyridin-4-yl)phenyl)-5-(2,2,2-trifluoroethoxy)-[1,2,4]triazolo[1,5-a]pyridin-2-amine (13.8 mg, 33%) | 2-bromo-8-(propan-2-yl)-5-(2,2,2-trifluoroethoxy)-[1,2,4]triazolo[1,5-a]pyridine (intermediate 3.4) (30 mg, 88.7 µmol) and 3-methoxy-4-(2-methyl-4-pyridyl)aniline (19 mg, 88.7 µmol), intermediate 2.02, below) | |

Synthesis of intermediates employed in table above of examples 17 to 21:

Intermediate 2.8 Used in Example 17

(8 endo)-3-(6-methoxypyridazin-4-yl)-3-azabicyclo[3.2.1]octan-8-amine

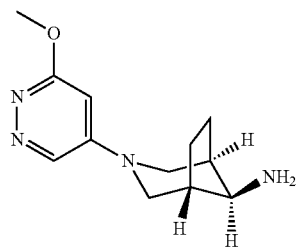 [SMILES: COc1cc(N2C[C@H]3CC[C@@H](C2)[C@@H]3N)cnn1]

Step 1 tert-Butyl ((8-endo)-3-(6-methoxypyridazin-4-yl)-3-azabicyclo[3.2.1]octan-8-yl)carbamate

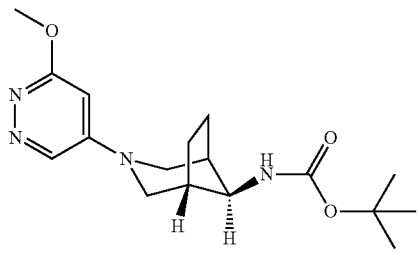 [SMILES: COc1cc(N2CC3CC[C@@H](C2)[C@@H]3NC(=O)OC(C)(C)C)cnn1]

Tert-butyl ((8 endo)-3-(6-chloropyridazin-4-yl)-3-azabicyclo[3.2.1]octan-8-yl)carbamate (4.314 g, 12.1 mmol), material of example 7, step 1, was partially dissolved in 150 l of methanol. The vial was flushed with argon. A sodium methoxide solution, 25 in methanol (7.94 g, 8.4 ml, 36.7 mmol) was added dropwise, the vial was flushed again with argon and closed. The reaction mixture was stirred at 85° C. overnight. The LC/MS showed still starting material. The reaction mixture was cooled to room temperature. Sodium methoxide solution, 25% in methanol (2.65 g, 2.8 ml, 12.2 mmol) was added and the reaction mixture was stirred at 85° C. for further six days. The reaction mixture was cooled to room temperature and then adsorbed on ISOLUTE HM-N and chromatographed over 120 g of silica gel with EtOAc in heptane, 0-100%. All fractions containing product were combined and concentrated to afford the title compound (2.423 g, 7.25 mmol, 59.9% yield) as an off-white solid. MS ES+ (m/z): 335.2 [(M+H)+].

Step 2

(8 endo)-3-(6-methoxypyridazin-4-yl)-3-azabicyclo[3.2.1]octan-8-amine

Tert-butyl ((8-endo)-3-(6-methoxypyridazin-4-yl)-3-azabicyclo[3.2.1]octan-8-yl)carbamate (500 mg, 1.5 mmol) and TFA (3.4 g, 2.3 mL, 29.9 mmol) were combined in DCM (10 ml). The reaction mixture was stirred at RT for 1 hr. LCMS check showed mostly conversion to product. The reaction mixture was evaporated under high vacuum, re-dissolved in DCM and washed once with saturated aqueous $K_2CO_3$. The aqueous layer was extracted twice with DCM. The aqueous phase was extracted further 6 times with MeOH:DCM, 5%. The organic layers were combined, dried over sodium sulfate and evaporated under vacuum to afford (the title compound (338 mg, 1.44 mmol, 96.5% yield) as an off-white solid. MS (ESI): m/z=235.2 [M+H]+.

Intermediate 2.9 Used in Example 18

(8-endo)-3-(3-methyl-1,2,4-oxadiazol-5-yl)-3-azabicyclo[3.2.1]octan-8-amine

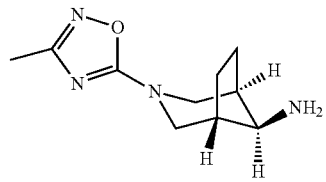

Step 1 tert-butyl N-[(8-endo)-3-cyano-3-azabicyclo[3.2.1]octan-8-yl]carbamate

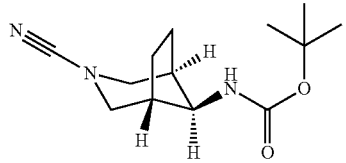 [SMILES: CC(C)(C)OC(=O)N[C@@H]1[C@@H]2CC[C@H]1CN(C#N)C2]

To a light yellow solution of tert-butyl (8-endo)-3-azabicyclo[3.2.1]octan-8-ylcarbamate (400 mg, 1.77 mmol) in etOH (8 ml) was added sodium bicarbonate (163 mg, 1.94 mmol), followed by cyanogen bromide (206 mg, 102 μl, 1.94 mmol). The reaction mixture was stirred over night at room temp. TLC and LC-MS showed the reaction was complete. The suspension was filtered off and washed with some ethanol. The crude reaction mixture was concentrated in vacuo. The crude material was purified by flash chromatography (silica gel, 25 g, 0% to 100% EtOAc in heptane) to afford the title compound as a light yellow powder (376 mg, 1.5 mmol, 84.6% yield). MS ES+ (m/z): 252.2 [(M+H)+].

Step 2

(8-endo)-3-(3-methyl-1,2,4-oxadiazol-5-yl)-3-azabicyclo[3.2.1]octan-8-amine

To a light yellow solution of tert-butyl ((8-endo)-3-cyano-3-azabicyclo[3.2.1]octan-8-yl)carbamate (350 mg, 1.39 mmol) in ethanol (5 ml) was added N-hydroxyacetamidine (124 mg, 1.67 mmol, Eq: 1.2). Then zinc chloride (228 mg, 1.67 mmol) dissolved in ethanol (1.5 ml) was added. The reaction mixture was stirred at room temp for 2 hours, HCl 37% (348 μl, 4.18 mmol) was added and mixture was stirred for further 4 hours at 60° C. LC-MS showed the reaction was complete. The crude reaction mixture was concentrated in vacuo. The residue was taken up with 25 ml saturated aqueous NaHCO₃ and extracted with DCM (3×25 ml). The organic layers were dried over Na₂SO₄ and concentrated in vacuo. The crude material was purified by flash chromatography (silica gel, 10 g, 0% to 10% MeOH in DCM, at the end 7 M NH₃ in MeOH was used) to afford the title compound as an off-white powder (242 mg, 1.16 mmol, 83.4% yield). MS ES+ (m/z): 209.1 [(M+H)+].

Intermediate 2.01 Used in Example 19

3-Methoxy-4-(3-methyl-1,2,4-triazol-1-yl)aniline

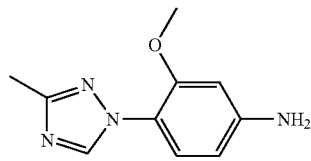

The compound was prepared as described by K. H. Baumann et al. in patent US2009/215759 A1.

Intermediate 2.02 Used in Example 20

5-Amino-2-(4-methylimidazol-1-yl)benzonitrile

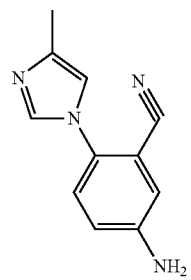

The material was prepared as described by K. H. Baumann et al. in patent US2009/181965 A1.

Intermediate 2.03 Used in Example 21

3-methoxy-4-(2-methyl-4-pyridyl)aniline

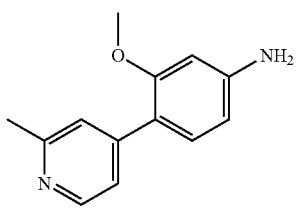 [SMILES: COc1cc(N)ccc1-c1ccnc(C)c1]

The synthesis of the compound is described by H. J. Gijsen et al. in patent WO2010/89292 A1, 2010.

EXAMPLE 22

2-[2-[[(8 endo)-3-(6-methylpyrimidin-4-yl)-3-azabicyclo[3.2.1]octan-8-yl]amino]-5-[(1S)-2,2,2-trifluoro-1-methyl-ethoxy]-[1,2,4]triazolo[1,5-a]pyridin-8-yl]propan-2-ol

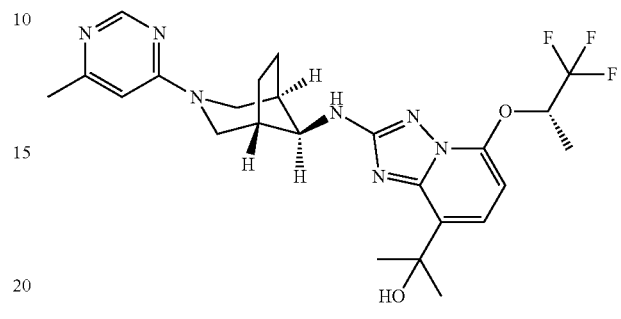

Intermediate 3.5

2-[2-bromo-5-[(1S)-2,2,2-trifluoro-1-methyl-ethoxy]-[1,2,4]triazolo[1,5-a]pyridin-8-yl]propan-2-ol

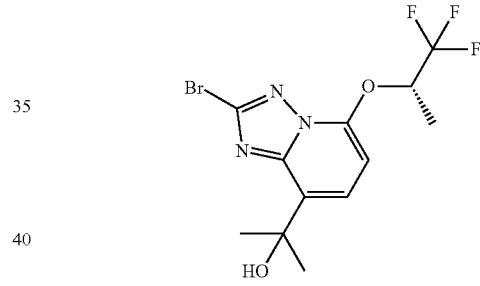

Step 1

Methyl 2-amino-6-{[(2S)-1,1,1-trifluoropropan-2-yl]oxy}pyridine-3-carboxylate

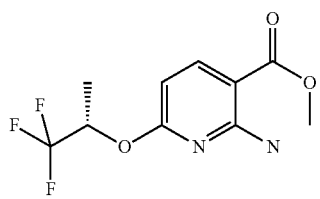 [SMILES: COC(=O)c1ccc(O[C@@H](C)C(F)(F)F)nc1N]

To a stirred solution of 2-amino-6-chloro-nicotinic acid methyl ester (2 g, 10.75 mmol) in DMF (10.0 ml) were added potassium tert-butoxide (3.01 g, 26.88 mmol) and (2S)-1,1,1-trifluoropropan-2-ol (2.45 g, 21.50 mmol) followed by Cu(I)Br (0.71 g, 5.37 mmol) at 0° C. The reaction mixture was stirred at 120° C. for 48 h. TLC/LC-MS indicated formation of desired product. The reaction mixture was filtered through celite and washed with ethyl acetate.

Thus obtained ethyl acetate was washed with water and brine. The organic layer was dried over anhydrous Na₂SO₄, filtered and concentrated to dryness. The obtained crude compound was purified by flash column chromatography, eluted with 20% ethyl acetate in hexane to give the title compound (1.25 g, 44%) as a sticky solid. MS ES+ (m/z): 264.8 [(M+H)+].

Step 2

2-(2-amino-6-{[(2S)-1,1,1-trifluoropropan-2-yl]oxy}pyridin-3-yl)propan-2-ol

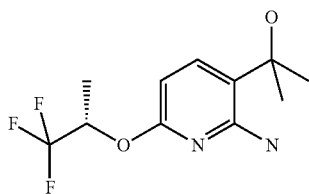 [SMILES: C[C@H](Oc1ccc(C(C)(C)O)c(N)n1)C(F)(F)F]

To a stirred solution of 2-amino-6-((S)-2,2,2-trifluoro-1-methyl-ethoxy)-nicotinic acid methyl ester (800 mg, 3.03 mmol) in THF (10 ml) was added methyl magnesium bromide (6.6 ml) at −25° C. The resultant reaction mixture was stirred at the same temperature for 1 h. The reaction mixture was slowly allowed to warm to room temperature and stirred at 25° C. for 18 h. The reaction mixture was then quenched with saturated aqueous ammonium chloride solution and extracted with ethyl acetate, washed with water and brine. The organic layer was dried over anhydrous Na₂SO₄, filtered and concentrated to dryness. Crude was purified by flash column chromatography, eluted with 20% ethyl acetate and hexane to afford the title compound (580 mg, 72%) as a liquid. MS ES+ (m/z): 264.8 [(M+H)+].

Step 3

Ethyl N-{[3-(2-hydroxypropan-2-yl)-6-{[(2S)-1,1,1-trifluoropropan-2-yl]oxy}pyridin-2-yl]carbamothioyl}carbamate

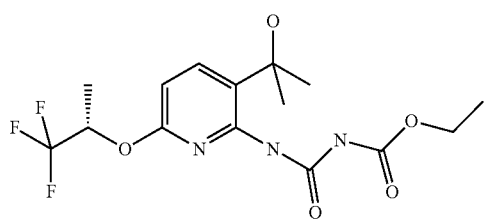 [SMILES: CCOC(=O)NC(=O)Nc1nc(O[C@@H](C)C(F)(F)F)ccc1C(C)(C)O]

To a stirred solution of 2-(2-amino-6-{[(2S)-1,1,1-trifluoropropan-2-yl]oxy}pyridin-3-yl)propan-2-ol (2.0 g, 7.576 mmol) in dioxane (12 ml) was added ethoxycarbonyl-isothiocyanate (1.7 g, 15.15 mmol) at 25° C. The resultant reaction mixture was stirred at 25° C. for 2 h. TLC and LCMS showed that staring material product was formed. The solvent was evaporated, azeotroped with toluene (3×20 ml). The crude product (2.2 g crude) obtained as a light brown solid was directly used in the next step. MS ES+ (m/z): 395.6 [(M+H)+].

Step 4

2-(2-amino-5-{[(2S)-1,1,1-trifluoropropan-2-yl]oxy}-[1,2,4]triazolo[1,5-a]pyridin-8-yl)propan-2-ol

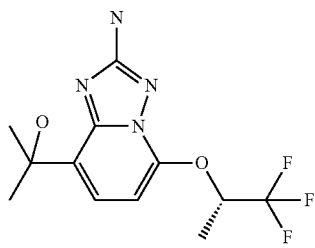 [SMILES: C[C@H](Oc1ccc(C(C)(C)O)c2nc(N)nn12)C(F)(F)F]

To a stirred solution of ethyl N-{[3-(2-hydroxypropan-2-yl)-6-{[(2S)-1,1,1-trifluoropropan-2-yl]oxy}pyridin-2-yl]carbamothioyl}carbamate (2.1 g, 5.316 mmol) in ethanol (12 ml) were added hydroxyl amine hydrochloride (0.92 g, 13.29 mmol) and DIPEA (3.76 ml, 21.26 mmol) at 0° C. The reaction mixture was reflux for 3 h. The reaction mass was concentrated under vacuum to provide crude material crude which was purified by flash column chromatography to afford the title compound (1.1 g, 50% two step yield) as a white solid. MS ES+ (m/z): 304.7 [(M+H)+].

Step 5

2-(2-bromo-5-{[(2S)-1,1,1-trifluoropropan-2-yl]oxy}-[1,2,4]triazolo[1,5-a]pyridin-8-yl)propan-2-ol

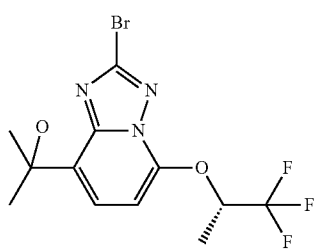 [SMILES: C[C@H](Oc1ccc(C(C)(C)O)c2nc(Br)nn12)C(F)(F)F]

To a stirred solution of 2-(2-amino-5-{[(2S)-1,1,1-trifluoropropan-2-yl]oxy}-[1,2,4]triazolo[1,5-a]pyridin-8-yl)propan-2-ol (700 mg, 2.3 mmol) in water (3 ml), was added 47% HBr (3 ml), followed by sodium nitrite (317 mg, 4.60 mmol in water, 1 ml) at 0° C. for 10 minutes. The reaction mixture was stirred at 0° C. for 20 minutes then Cu(II)B (776.7 mg, 3.46 mmol) was added at 0° C. and the reaction mixture was stirred at 25° C. for 17 h. It was then extracted with ethyl acetate (3×70 ml). The organic layer was washed with saturated aqueous, sodium bicarbonate solution (50 ml), water (40 ml) and brine (50 ml), dried over Na₂SO₄ filtered and evaporated in vacuum. The residue was purified by flash column chromatography to afford the title compound (430 mg, 51%) as an off white solid. MS ES+ (m/z): 367.8 [(M+H)+].

Step 6, Final Coupling

2-[2-[[(8 endo)-3-(6-methylpyrimidin-4-yl)-3-azabicyclo[3.2.1]octan-8-yl]amino]-5-[(1S)-2,2,2-trifluoro-1-methyl-ethoxy]-[1,2,4]triazolo[1,5-a]pyridin-8-yl]propan-2-ol

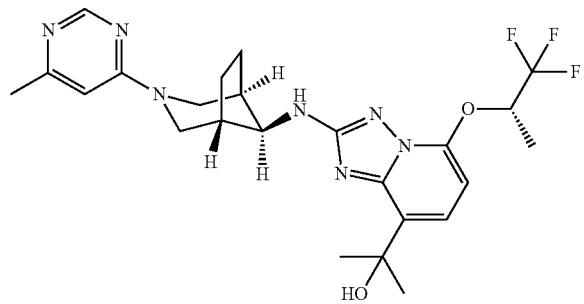 [SMILES: Cc1cc(N2C[C@H]3CC[C@@H](C2)[C@@H]3Nc2nc3c(C(C)(C)O)ccc(O[C@@H](C)C(F)(F)F)n3n2)ncn1]

The title compound, was prepared by Buchwald coupling in analogy to example 1, from 2-(2-bromo-5-{[(2S)-1,1,1-trifluoropropan-2-yl]oxy}-[1,2,4]triazolo[1,5-a]pyridin-8-yl)propan-2-ol (35 mg, 95.1 µmol), (8 endo)-3-(6-methylpyrimidin-4-yl)-3-azabicyclo[3.2.1]octan-8-amine (20.8 mg, 95.1 µmol), intermediate 2.3, example 4, with $Pd_2(dba)_3 \cdot CHCl_3$ (8.71 mg, 9.51 µmol) in the presence of sodium tert-butoxide and Xanthphos in a microwave at 120° C. during 20 min. The title compound was obtained as a white foam (5 mg, 10.4% yield). HR-MS ES+ (m/z): 506.2488 [(M+H)+].

EXAMPLES 23-27

According to the coupling procedure described in example 22 step 6, further derivatives have been prepared by Buchwald coupling from the respective intermediate 3.5 and intermediates 2 as comprised in the table below and described below:

| Examples number | Structure | Systematic name Yield of reaction | Starting materials | MW found $(M + H)^+$(HR) |
|---|---|---|---|---|
| 23 | | 2-[2-[[(8 endo)-3-(6-chloropyridazin-4-yl)-3-azabicyclo[3.2.1]octan-8-yl]amino]-5-[(1S)-2,2,2-trifluoro-1-methyl-ethoxy]-[1,2,4]triazolo[1,5-a]pyridin-8-yl]propan-2-ol (9.5 mg, 19%) | 2-(2-bromo-5-{[(2S)-1,1,1-trifluoropropan-2-yl]oxy}-[1,2,4]triazolo[1,5-a]pyridin-8-yl)propan-2-ol (intermediate 3.5) (35 mg, 95.1 µmol) and (8-endo)-3-(6-chloropyridazin-4-yl)-3-azabicyclo[3.2.1]octan-8-amine (22.7 mg, 95.1 µmol), intermediate 2.6, example 7 | 526.1940 |
| 24 | | 2-[2-[3-methoxy-4-(3-methyl-1,2,4-triazol-1-yl)anilino]-5-[(1S)-2,2,2-trifluoro-1-methyl-ethoxy]-[1,2,4]triazolo[1,5-a]pyridin-8-yl]propan-2-ol (18 mg, 33.3%) | 2-(2-bromo-5-{[(2S)-1,1,1-trifluoropropan-2-yl]oxy}-[1,2,4]triazolo[1,5-a]pyridin-8-yl)propan-2-ol (intermediate 3.5) (40.5, 110 µmol) and 3-methoxy-4-(3-methyl-1,2,4-triazol-1-yl)aniline (22.5 mg, 110 µmol), intermediate 2.01 of example 19 | 492.1983 |
| 25 | | 2-[2-[4-(4-chloroimidazol-1-yl)-3-methoxy-anilino]-5-[(1S)-2,2,2-trifluoro-1-methyl-ethoxy]-[1,2,4]triazolo[1,5-a]pyridin-8-yl]propan-2-ol (17.3 mg, 31.2%) | 2-(2-bromo-5-{[(2S)-1,1,1-trifluoropropan-2-yl]oxy}-[1,2,4]triazolo[1,5-a]pyridin-8-yl)propan-2-ol (intermediate 3.5) (40 mg, 109 µmol) and 4-(4-chloroimidazol-1-yl)-3-methoxy-aniline (24.3 mg, 109 µmol), intermediate 2.04, below. | 511.1476 |

| Examples number | | Systematic name Yield of reaction | Starting materials | MW found (M + H)⁺(HR) |
|---|---|---|---|---|
| 26 | (structure shown) | 2-[2-[4-(3-chloro-1,2,4-triazol-1-yl)-3-methoxy-anilino]-5-[(1S)-2,2,2-trifluoro-1-methyl-ethoxy]-[1,2,4]triazolo[1,5-a]pyridin-8-yl]propan-2-ol (55.6 mg, 49.8%) | 2-(2-bromo-5-{[(2S)-1,1,1-trifluoropropan-2-yl]oxy}-[1,2,4]triazolo[1,5-a]pyridin-8-yl)propan-2-ol (intermediate 3.5) (40 mg, 109 µmol) and 4-(3-chloro-1,2,4-triazol-1-yl)-3-methoxy-aniline (24.4 mg, 109 µmol), intermediate 2.05, below. | 512.1422 |
| 27 | (structure shown) | 5-[[8-(2-hydroxypropan-2-yl)-5-[(1S)-2,2,2-trifluoro-1-methyl-ethoxy]-[1,2,4]triazolo[1,5-a]pyridin-2-yl]amino]-2-(4-methylimidazol-1-yl)benzonitrile (25.9 mg, 49.1%) | 2-(2-bromo-5-{[(2S)-1,1,1-trifluoropropan-2-yl]oxy}-[1,2,4]triazolo[1,5-a]pyridin-8-yl)propan-2-ol (intemediate 3.5) (40 mg, 109 µmol) and 5-amino-2-(4-methylimidazol-1-yl)benzonitrile (20 mg, 109 µmol), intermediate 2.02, example 20. | 486.186 |

Synthesis of intermediates employed in table above of examples 23 to 27:

Intermediate 2.04 Used in Example 25

4-(4-chloroimidazol-1-yl)-3-methoxy-aniline

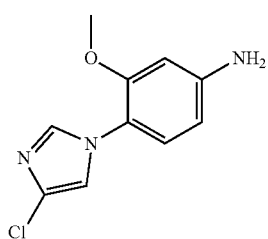

The synthesis of the compound is described by L. R. Marcin in patent WO2010/83141 A1.

Intermediate 2.05 Used in Example 26

4-(3-chloro-1,2,4-triazol-1-yl)-3-methoxy-aniline

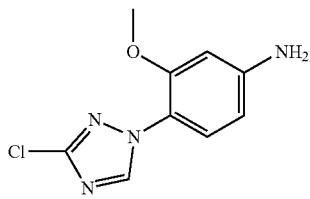

The synthesis of the compound is described by L. R. Marcin in patent WO2010/83141 A1.

EXAMPLE 28

8-isopropyl-N-((8 endo)-3-(2-methoxypyridin-4-yl)-3-azabicyclo[3.2.1]octan-8-yl)-5-(((S)-1,1,1-trifluoropropan-2-yl)oxy)-[1,2,4]triazolo[1,5-a]pyridin-2-amine

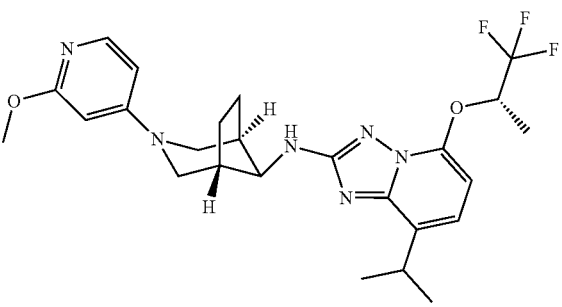 [SMILES: COc1cc(N2C[C@H]3CC[C@@H](C2)C3Nc2nc3c(C(C)C)ccc(O[C@@H](C)C(F)(F)F)n3n2)ccn1]

Intermediate 3.6

2-bromo-8-isopropyl-5-[(1S)-2,2,2-trifluoro-1-methyl-ethoxy]-[1,2,4]triazolo[1,5-a]pyridine

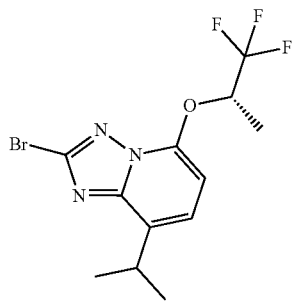 [SMILES: CC(C)c1ccc(O[C@@H](C)C(F)(F)F)n2nc(Br)nc12]

Step 1

2-bromo-8-isopropyl-5-[(1S)-2,2,2-trifluoro-1-methyl-ethoxy]-[1,2,4]triazolo[1,5-a]pyridine To a stirred solution of 2-[2-bromo-5-((S)-2,2,2-trifluoro-1-methyl-ethoxy)-[1,2,4]triazolo[1,5-a]pyridin-8-yl]-propan-2-ol, intermediate 3.5, example 22, (500 mg, 1.64 mmol) in TFA (8 ml) was added, tri-ethysilane (4 ml) at 0° C. The resultant reaction mixture was stirred at 25° C. for 20 h. The pH of the reaction mixture was adjusted to 8 by using saturated aqueous sodium bicarbonate solution. The aqueous layer was extracted with ethyl acetate (250 ml). The organic layer was washed with water (25 ml) and brine (50 ml). The obtained organic layer was dried over anhydrous $Na_2SO_4$, filtered and concentrated to dryness. The crude compound was purified by column chromatography, eluted with 10% ethyl acetate in hexane to get the desired compound (220 mg, 45%) as a white solid. MS ES+ (m/z): 351.9 [(M+H)+].

Step 2, Coupling Step 8-isopropyl-N-((8 endo)-3-(2-methoxypyridin-4-yl)-3-azabicyclo[3.2.1]octan-8-yl)-5-(((S)-1,1,1-trifluoropropan-2-yl)oxy)-[1,2,4]triazolo[1,5-a]pyridin-2-amine

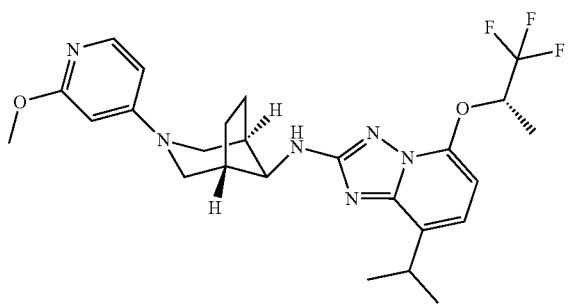 [SMILES: COc1cc(N2C[C@H]3CC[C@@H](C2)C3Nc2nc3c(C(C)C)ccc(O[C@@H](C)C(F)(F)F)n3n2)ccn1]

The title compound, was prepared by Buchwald coupling in analogy to example 1 from 2-bromo-8-(propan-2-yl)-5-{[(2S)-1,1,1-trifluoropropan-2-yl]oxy}-[1,2,4]triazolo[1,5-a]pyridine (35 mg, 95.1 μmol), (8-endo)-3-(2-methoxy-4-pyridyl)-3-azabicyclo[3.2.1]octan-8-amine (40 mg, 114 μmol) (intermediate 2.5, example 6) with $Pd_2(dba)_3 \cdot CHCl_3$ (10.4 mg, 11.4 μmol) in the presence of sodium tert-butoxide and Xanthphos in a microwave at 120° C. during 20 min. The title compound was obtained as a white solid (48 mg, 83.3% yield). MS ES+ (m/z): 505.3 [(M+H)+].

EXAMPLES 29-33

According to the coupling procedure described in example 28 step 2, further derivatives have been prepared by Buchwald coupling from the respective intermediate 3.6 and intermediates 2 as comprised in the table below and described below:

| Examples number | Systematic name Yield of reaction | Starting materials | MW found (M + H)+(HR) |
|---|---|---|---|
| 29 | 8-isopropyl-N-((8 endo)-3-(6-methoxypyridazin-4-yl)-3-azabicyclo[3.2.1]octan-8-yl)-5-(((S)-1,1,1-trifluoropropan-2-yl)oxy)-[1,2,4]triazolo[1,5-a]pyridin-2-amine (23.6 mg, 46.7%) | 2-bromo-8-isopropyl-5-[(1S)-2,2,2-trifluoro-1-methyl-ethoxy]-[1,2,4]triazolo[1,5-a]pyridine (35.2 mg, 100 μmol) and (8 endo)-3-(6-methoxypyridazin-4-yl)-3-azabicyclo[3.2.1]octan-8-amine (23.4 mg, 100 μmol) intermediate 2.8, example 17. | 506.2495 |

| Examples number | Systematic name<br>Yield of reaction | Starting materials | MW found<br>(M + H)⁺(HR) |
|---|---|---|---|
| 30 | N-((8 endo)-3-(6-chloropyridazin-4-yl)-3-azabicyclo[3.2.1]octan-8-yl)-8-isopropyl-5-(((S)-1,1,1-trifluoropropan-2-yl)oxy)-[1,2,4]triazolo[1,5-a]pyridin-2-amine<br>(51 mg, 35.1%) | 2-bromo-8-isopropyl-5-[(1S)-2,2,2-trifluoro-1-methyl-ethoxy]-[1,2,4]triazolo[1,5-a]pyridine (35.2 mg, 100 µmol) and (8-endo)-3-(6-chloropyridazin-4-yl)-3-azabicyclo[3.2.1]octan-8-amine (23.9 mg, 100 µmol), intermediate 2.6, example 7. | 510.1966 |
| 31 | 8-isopropyl-N-[(8 endo)-3-(3-methyl-1,2,4-oxadiazol-5-yl)-3-azabicyclo[3.2.1]octan-8-yl]-5-[(1S)-2,2,2-trifluoro-1-methyl-ethoxy]-[1,2,4]triazolo[1,5-a]pyridin-2-amine<br>(25.7 mg, 47.2%) | 2-bromo-8-isopropyl-5-[(1S)-2,2,2-trifluoro-1-methyl-ethoxy]-[1,2,4]triazolo[1,5-a]pyridine (40 mg, 114 µmol) and (8-endo)-3-(3-methyl-1,2,4-oxadiazol-5-yl)-3-azabicyclo[3.2.1]octan-8-amine (23.7 mg, 114 µmol), intermediate 2.9, example 18 | 480.2337 |
| 32 | 8-isopropyl-N-[(8 endo)-3-(5-methyl-1,3,4-oxadiazol-2-yl)-3-azabicyclo[3.2.1]octan-8-yl]-5-[(1S)-2,2,2-trifluoro-1-methyl-ethoxy]-[1,2,4]triazolo[1,5-a]pyridin-2-amine<br>(30 mg, 59.6%) | 2-bromo-8-isopropyl-5-[(1S)-2,2,2-trifluoro-1-methyl-ethoxy]-[1,2,4]triazolo[1,5-a]pyridine (37 mg, 105 µmol) and (8 endo)-3-(5-methyl-1,3,4-oxadiazol-2-yl)-3-azabicyclo[3.2.1]octan-8-amine (21.9 mg, 105 µmol), intermediate 2.05, below). | 480.2356 |
| 33 | 8-isopropyl-N-[3-methoxy-4-(3-methyl-1,2,4-triazol-1-yl)phenyl]-5-[(1S)-2,2,2-trifluoro-1-methyl-ethoxy]-[1,2,4]triazolo[1,5-a]pyridin-2-amine<br>(19.6 mg, 32.2%) | 2-bromo-8-isopropyl-5-[(1S)-2,2,2-trifluoro-1-methyl-ethoxy]-[1,2,4]triazolo[1,5-a]pyridine (45 mg, 128 µmol) and 3-methoxy-4-(3-methyl-1,2,4-triazol-1-yl)aniline (26.1 mg, 128 µmol, intermediate 2.01 used in example 19. | 476.2036 |

Synthesis of intermediates employed in table above of examples 29 to 33:

Intermediate 2.05 of Example 32

(8 endo)-3-(5-methyl-1,3,4-oxadiazol-2-yl)-3-azabi-cyclo[3.2.1]octan-8-amine

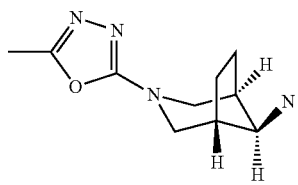

Step 1

Tert-butyl N-[(8 endo)-3-5-methyl-1,3,4-oxadiazol-2-yl)-3-azabicyclo[3.2.1]octan-8-yl]carbamate

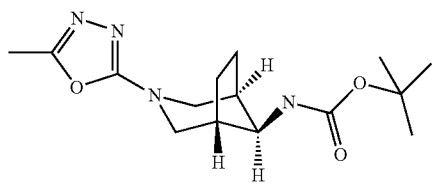 [SMILES: Cc1nnc(N2C[C@H]3CC[C@@H](C2)[C@@H]3NC(=O)OC(C)(C)C)o1]

To a solution of tert-butyl (8 endo)-3-azabicyclo[3.2.1]octan-8-ylcarbamate (200 mg, 884 µmol) in ethanol (10 ml), was added tri-ethylamine (358 mg, 493 µl, 3.53 mmol) followed by 2-bromo-5-methyl-1,3,4-oxadiazole (288 mg, 1.77 mmol). The reaction mixture was stirred at 130° C. for 12 h. The crude reaction mixture was concentrated in vacuum. Water was added and the aqueous phase was extracted with dichloromethane. The organic layers were dried over MgSO₄ and concentrated in vacuum. The crude material was purified by flash chromatography (0% to 5% MeOH in DCM) to afford the title as a white solid (230 mg, 84.4% yield).
MS ES+ (m/z): 309.2 [(M+H)⁺]

Step 2

(8 endo)-3-5-methyl-1,3,4-oxadiazol-2-yl)-3-azabi-cyclo[3.2.1]octan-8-amine

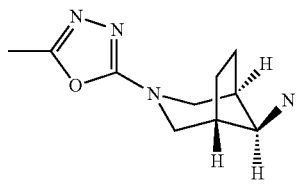

To a light yellow solution of tert-butyl (8 endo)-3-(5-methyl-1,3,4-oxadiazol-2-yl)-3-azabicyclo[3.2.1]octan-8-ylcarbamate (230 mg, 746 µmol) in dichloromethane (6 ml) was added trifluoroacetic acid (850 mg, 575 µl, 7.46 mmol).

The reaction mixture was stirred at room temperature for 12 h. TFA (85.0 mg, 57.5 µl, 746 µmol) was added and the mixture was further stirred for 3 hours. The reaction mixture was concentrated in vacuo, the crude material was purified by ion-exchange column chromatography, (Si-SCX-2, 10 g, washed with MeOH and liberated with MeOH (NH₃, 7 M)) to afford the title compound as a light yellow solid (124.5 mg, 80.2% yield). MS ES+ (m/z): 209.1 [(M+H)⁺]

EXAMPLE 34

N-[3-methoxy-4-(3-methyl-1,2,4-triazol-1-yl)phe-nyl]-8-(trifluoromethyl)-5-[(1S)-2,2,2-trifluoro-1-methyl-ethoxy]-[1,2,4]triazolo[1,5-a]pyridin-2-amine

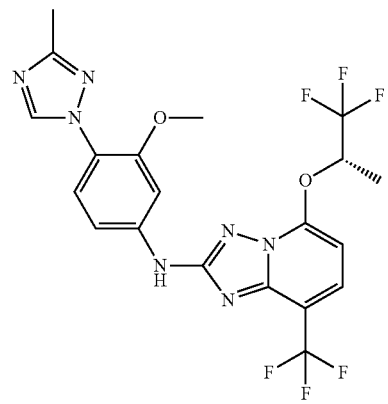 [SMILES: COc1cc(Nc2nc3c(C(F)(F)F)ccc(O[C@@H](C)C(F)(F)F)n3n2)ccc1-n1cnc(C)n1]

Intermediate 3.7

2-bromo-8-(trifluoromethyl)-5-{[(2S)-1,1,1-trifluo-ropropan-2-yl]oxy}-[1,2,4]triazolo[1,5-a]pyridine

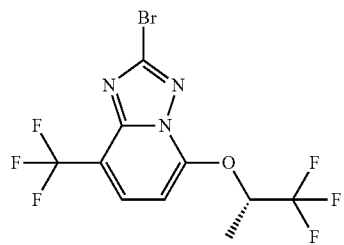 [SMILES: C[C@H](Oc1ccc(C(F)(F)F)c2nc(Br)nn12)C(F)(F)F]

Step 1

6-chloro-3-trifluoromethyl)pyridin-2-amine

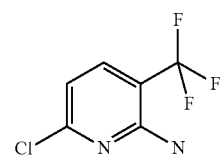 [SMILES: Nc1nc(Cl)ccc1C(F)(F)F]

2,6-Dichloro-3-(trifluoromethyl)pyridine (30 g, 139.53 mmol) in 28% aqueous ammonia (400 ml) was heated in an autoclave at 90° C. for 24 h. The reaction mass was brought to RT, diluted with water (200 ml) and the aqueous layer were extracted with DCM (3×500 ml). The combined organic layers were washed with brine (250 ml) dried and concentrated. The crude material was purified by flash chromatography on silica gel using 0-5% EtOAc-hexane as eluent to afford 6-chloro-3-(trifluoromethyl) pyridin-2-amine (4 g, 14.6%) as off white solid.

Step 2

3-(trifluoromethyl)-6-{[(2S)-1,1,1-trifluoropropan-2-yl]oxy}pyridin-2-amine

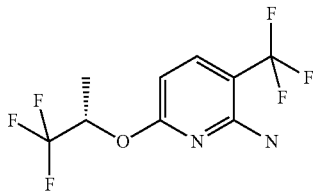 [SMILES: C[C@H](Oc1ccc(C(F)(F)F)c(N)n1)C(F)(F)F]

To a stirred solution of 6-chloro-3-trifluoromethyl-pyridin-2-ylamine (2 g, 10.753 mmol) in DMF (10 ml) were added potassium tert-butoxide (2.4 g, 21.50 mmol) and (2S)-1,1,1-trifluoropropan-2-ol (2.45 g, 21.50 mmol) followed by Cu(I)Br (0.7 g, 21.50 mmol) at 25° C. under argon. The reaction mixture was stirred at 120° C. for 48 h as TLC/LC-MS indicated formation of desired product. The reaction mixture was filtered through a celite bed and washed with ethyl acetate. The obtained ethyl acetate was washed with water and brine. The organic layer was dried over anhydrous Na$_2$SO$_4$, filtered and concentrated to dryness. The obtained crude material was purified by flash column chromatography, eluted with 20% ethyl acetate in hexane to afford the title compound (1.2 g, 42%) as a sticky solid. MS ES+ (m/z): 264.7 [(M+H)$^+$]

Step 3

Ethyl N-{[3-trifluoromethyl)-6-{[(2S)-1,1,1-trifluoropropan-2-yl]oxy}pyridin-2-yl]carbamothioyl}carbamate

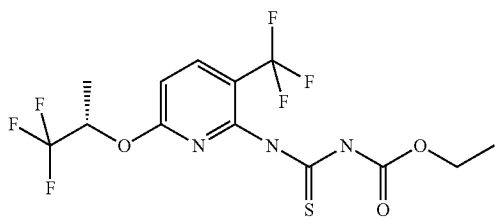 [SMILES: CCOC(=O)NC(=S)Nc1nc(O[C@@H](C)C(F)(F)F)ccc1C(F)(F)F]

To a stirred solution of 3-trifluoromethyl-6-((S)-2,2,2-trifluoro-1-methyl-ethoxy)-pyridin-2-ylamine (1.0 g, 3.663 mmol) in dioxane (2 ml) was added ethoxycarbonyl-isothiocyanate (0.82 mg, 7.326 mmol) at 25° C. The resultant reaction mixture was stirred at 25° C. for 2 h. TLC and LCMS showed that product had formed. The solvent was evaporated and the obtained crude material was azeotroped with toluene (3×20 ml) to give title compound (1.2 g, Crude) as a sticky solid which was used directly in the in next step without purification. MS ES+ (m/z): 405.8 [(M+H)$^+$]

Step 4

8-(trifluoromethyl)-5-{[(2S)-1,1,1-trifluoropropan-2-yl]oxy}-[1,2,4]triazolo[1,5-a]pyridin-2-amine

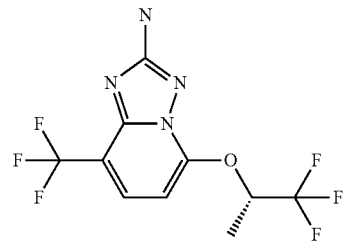

To a stirred solution of ethyl N-{[3-(trifluoro methyl)-6-{[(2S)-1,1,1-trifluoropropan-2-yl]oxy}pyridin-2-yl]carbamo-thionyl}-carbamate (1.25 g, 0.445 mmol) in ethanol (5 ml) were added hydroxylamine hydrochloride (0.51 g, 7.40 mmol) and DIPEA (2.1 ml, 11.85 mmol) at 25° C. The resultant reaction mixture was reflux for 4 h. It was then concentrated under reduced pressure to get crude material, which was purified by flash column chromatography to afford the title compound (800 mg, 68% two step yield) as an off white solid. MS ES+ (m/z): 315.3 [(M+H)$^+$]

Step 5

2-bromo-8-(trifluoromethyl)-5-{[(2S)-1,1,1-trifluoropropan-2-yl]oxy}-[1,2,4]triazolo[1,5-a]pyridine

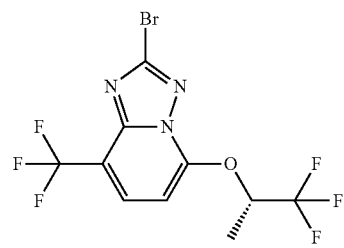 [SMILES: C[C@H](Oc1ccc(C(F)(F)F)c2nc(Br)nn12)C(F)(F)F]

To a stirred solution of 8-trifluoromethyl-5-((S)-2,2,2-trifluoro-1-methyl-ethoxy)-[1,2,4]triazolo[1,5-a]pyridin-2-ylamine (800 mg, 2.548 mmol) in water (5 ml) was added 47% HBr (5 ml), followed by sodium nitrite (351 mg, 5.09 mmol) at 0° C. over a period of 10 min. The reaction mass was stirred for 20 min, Cu(II)Br (852 mg, 3.822 mmol) was added and the mixture was then stirred at 25° C. for 17 h. It was extracted with ethyl acetate (3×70 ml), the organic layer was washed with saturated aqueous sodium bicarbonate solution (50 ml), water (40 ml) and brine (50 ml). The organic layer was dried over Na$_2$SO$_4$ filtered and evaporated in reduced pressure to get the crude material which was purified by flash column chromatography, eluted with 20% ethyl acetate in hexane to afford the title compound (700 mg, 72%) as a sticky solid. MS ES+ (m/z): 379.7 [(M+H)$^+$]

Step 6, Final Coupling

N-[3-methoxy-4-(3-methyl-1,2,4-triazol-1-yl)phenyl]-8-(trifluoromethyl)-5-[(1S)-2,2,2-trifluoro-1-methyl-ethoxy]-[1,2,4]triazolo[1,5-a]pyridin-2-amine

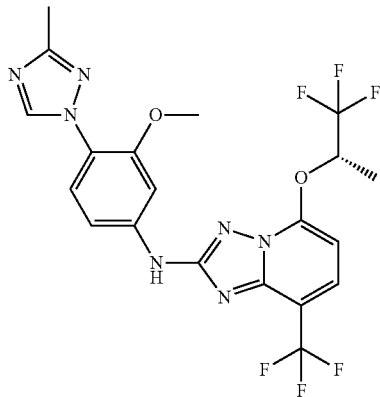 [SMILES: COc1cc(Nc2nc3c(C(F)(F)F)ccc(O[C@@H](C)C(F)(F)F)n3n2)ccc1-n1cnc(C)n1]

The title compound, was prepared by Buchwald coupling in analogy to example 1, from 2-bromo-8-(trifluoromethyl)-5-{[(2S)-1,1,1-trifluoropropan-2-yl]oxy}-[1,2,4]triazolo[1,5-a]pyridine (45 mg, 119 µmol), 3-methoxy-4-(3-methyl-1H-1,2,4-triazol-1-yl)aniline (24.3 mg, 119 µmol) (intermediate 2.01, example 19) with $Pd_2(dba)_3 \cdot CHCl_3$ (10.9 mg, 11.9 µmol) in the presence of sodium tert-butoxide and Xanthphos in a microwave at 120° C. during 20 min. It was obtained as a off-white solid (10.5 mg, 17.6% yield). HR-MS ES+ (m/z): 502.1436 [(M+H)+].

EXAMPLE 35

N-[4-(4-chloroimidazol-1-yl)-3-methoxy-phenyl]-8-(trifluoromethyl)-5-[(1S)-2,2,2-trifluoro-1-methyl-ethoxy]-[1,2,4]triazolo[1,5-a]pyridin-2-amine

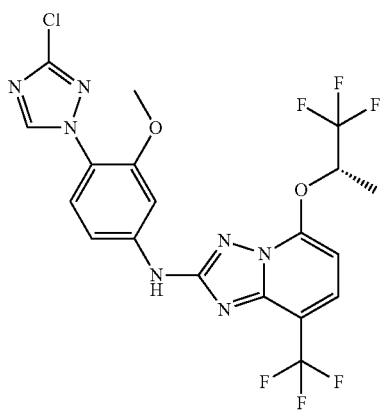 [SMILES: COc1cc(Nc2nc3c(C(F)(F)F)ccc(O[C@@H](C)C(F)(F)F)n3n2)ccc1-n1cnc(Cl)n1]

The title compound, was prepared by Buchwald coupling in analogy to example 1, from 2-bromo-8-(trifluoromethyl)-5-{[(2S)-1,1,1-trifluoropropan-2-yl]oxy}-[1,2,4]triazolo[1,5-a]pyridine (37.8 mg, 100 µmol), intermediate 3.7, example 34, 4-(4-chloroimidazol-1-yl)-3-methoxy-aniline (22.4 mg, 100 µmol), intermediate 2.04 used in example 25, with $Pd_2(dba)_3 \cdot CHCl_3$ (9.16 mg, 10 µmol) in the presence of sodium tert-butoxide and Xanthphos in a microwave at 120° C. during 20 min. It was obtained as a off-white solid (4.5 mg, 8.64% yield). HR-MS ES+ (m/z): 521.0924 [(M+H)+].

The heterocycles halides are either commercial available, known in the literature so they can be prepared by methods known in the art or alternatively could be prepared as described in the specification.

The compounds were investigated in accordance with the test given hereinafter.

Description of γ-Secretase Assay

Cellular γ-Secretase Assay

Human neuroglioma H4 cells overexpressing human APP695 with the Swedish double mutation (K595N/M596L) were plated at 30,000 cells/well/100 µl in 96-well plates in IMDM media containing 10% FCS, 0.2 mg/l Hygromycin B and incubated at 37° C., 5% $CO_2$.

3-4 hr post plating, compounds are a diluted in media and 50 µl is added as 1.5-fold concentrate to achieve the final concentration. Compound incubation is performed for 24 hr. Final doses typically range from 4 µM down to 0.0013 µM in half-log steps resulting in a eight point dose response curve.

Appropriate controls using vehicle only and reference compound were applied to this assay. The final concentration of $Me_2SO$ was 0.4%.

After incubation at 37° C., 5% $CO_2$, the supernatant was subjected to quantification of secreted Aβ42 by the means of an AlphaLisa assay kit (Human Amyloid beta 1-42 Kit: Cat #AL203C, Perkin Elmer). 20 µl of the cell culture supernatant was transferred to an assay plate. Then 10 µl of a mixture of the AlphaLisa coupled capture antibody and the biotinylated detection antibody was added and incubated for 3 hours at room temperature while softly shaking the assay plate. After a further addition of 20 µl of the Donor beads the assay plate was incubated for 30 min at room temperature and constant shaking without exposure to direct light. The assay plate was then read on a Paradigm AlphaLisa Reader using the build-in program with excitation at 680 nm and emission at 570 nm.

The measured signals were then used to calculate $IC_{50}$ values for inhibition of Aβ42 secretion by nonlinear regression fit analysis using XLfit 5.3 software (IDBS).

In the list below are described the data for all compounds to the inhibition of Aβ42 secretion (nM):

| Example No. | $EC_{50}$ Aβ42 (uM) |
|---|---|
| 1 | 0.0436 |
| 2 | 0.0070 |
| 3 | 0.0206 |
| 4 | 0.0299 |
| 5 | 0.0092 |
| 6 | 0.0156 |
| 7 | 0.0465 |
| 8 | 0.0448 |
| 9 | 0.0438 |
| 10 | 0.0455 |
| 11 | 0.0332 |
| 12 | 0.0385 |
| 13 | 0.0117 |
| 14 | 0.0254 |
| 15 | 0.0232 |
| 16 | 0.0342 |
| 17 | 0.0212 |

-continued

| Example No. | EC$_{50}$ Aβ42 (uM) |
|---|---|
| 18 | 0.0374 |
| 19 | 0.0266 |
| 20 | 0.0494 |
| 21 | 0.0212 |
| 22 | 0.0346 |
| 23 | 0.0400 |
| 24 | 0.0390 |
| 25 | 0.0270 |
| 26 | 0.0422 |
| 27 | 0.0373 |
| 28 | 0.0196 |
| 29 | 0.0142 |
| 30 | 0.0132 |
| 31 | 0.0490 |
| 32 | 0.0432 |
| 33 | 0.0390 |
| 34 | 0.0405 |
| 35 | 0.0314 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions. The administration can also be effected topically, e.g. transdermal administration, or in form of eye drops or ear drops.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the inhibition of Aβ42 secretion, such as of Alzheimer's disease.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | | |
|---|---|---|---|---|---|
| | | mg/tablet | | | |
| Item | Ingredients | 5 | 25 | 100 | 500 |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | mg/capsule | | | |
| Item | Ingredients | 5 | 25 | 100 | 500 |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I,

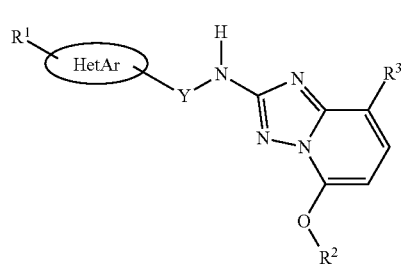

wherein:
HetAr is a five or six membered hetaryl group selected from the group consisting of:

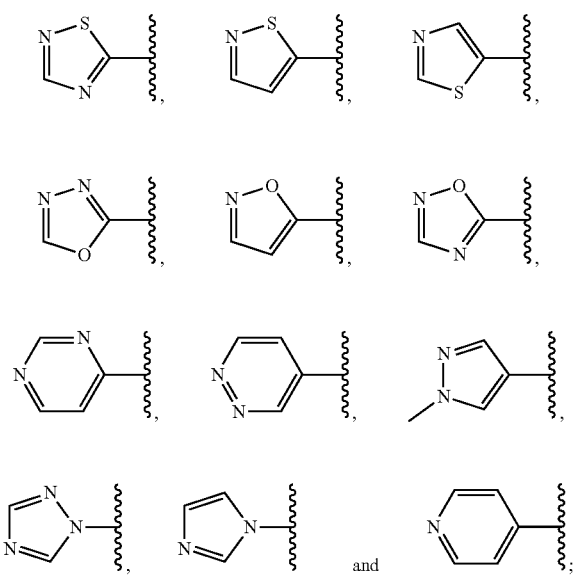

R¹ is hydrogen, lower alkyl, lower alkyl substituted by halogen, halogen or lower alkoxy;
R² is lower alkyl substituted by halogen;
R³ is hydrogen, lower alkyl substituted by halogen, lower alkyl or lower alkyl substituted by hydroxy;
Y is

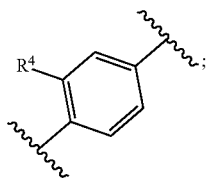

and
R⁴ is CN, lower alkoxy, or lower alkoxy substituted by halogen;
or a pharmaceutically active acid addition salt thereof, a racemic mixture or its corresponding enantiomers, optical isomers, or stereoisomers thereof.

2. A compound selected from the group consisting of:
2-(2-((3-(difluoromethoxy)-4-(3-methyl-1H-1,2,4-triazol-1-yl)phenyl)amino)-5-(2,2,2-trifluoroethoxy)-[1,2,4]triazolo[1,5-a]pyridin-8-yl)propan-2-ol;
N-(3-(difluoromethoxy)-4-(3-methyl-1H-1,2,4-triazol-1-yl)phenyl)-8-isopropyl-5-(2,2,2-trifluoroethoxy)-[1,2,4]triazolo[1,5-a]pyridin-2-amine;
8-Isopropyl-N-(3-methoxy-4-(3-methyl-1H-1,2,4-triazol-1-yl)phenyl)-5-(2,2,2-trifluoroethoxy)-[1,2,4]triazolo[1,5-a]pyridin-2-amine;
5-((8-isopropyl-5-(2,2,2-trifluoroethoxy)-[1,2,4]triazolo[1,5-a]pyridin-2-yl)amino)-2-(4-methyl-1H-imidazol-1-yl)benzonitrile;
8-isopropyl-N-(3-methoxy-4-(2-methylpyridin-4-yl)phenyl)-5-(2,2,2-trifluoroethoxy)-[1,2,4]triazolo[1,5-a]pyridin-2-amine;
2-[2-[3-methoxy-4-(3-methyl-1,2,4-triazol-1-yl)anilino]-5-[(1S)-2,2,2-trifluoro-1-methyl-ethoxy]-[1,2,4]triazolo[1,5-a]pyridin-8-yl]propan-2-ol;
2-[2-[4-(4-chloroimidazol-1-yl)-3-methoxy-anilino]-5-[(1S)-2,2,2-trifluoro-1-methyl-ethoxy]-[1,2,4]triazolo[1,5-a]pyridin-8-yl]propan-2-ol;
2-[2-[4-(3-chloro-1,2,4-triazol-1-yl)-3-methoxy-anilino]-5-[(1S)-2,2,2-trifluoro-1-methyl-ethoxy]-[1,2,4]triazolo[1,5-a]pyridin-8-yl]propan-2-ol;
5-[[8-(2-hydroxpropan-2-yl)-5-[(1S)-2,2,2-trifluoro-1-methyl-ethoxy]-[1,2,4]triazolo[1,5-a]pyridin-2-yl]amino]-2-(4-methylimidazol-1-yl)benzonitrile;
8-isopropyl-N-[3-methoxy-4-(3-methyl-1,2,4-triazol-1-yl)phenyl]-5-[(1S)-2,-2,2-trifluoro-1-methyl-ethoxy]-[1,2,4]triazolo[1,5-a]pyridin-2-amine;
N-[3-methoxy-4-(3-methyl-1,2,4-triazol-1-yl)phenyl]-8-(trifluoromethyl)-5-[(1S)-2,2,2-trifluoro-1-methyl-ethoxy]-[1,2,4]triazolo[1,5-a]pyridin-2-amine; and
N-[4-(4-chloroimidazol-1-yl)-3-methoxy-phenyl]-8-(trifluoromethyl)-5-[(1S)-2,2,2-trifluoro-1-methyl-ethoxy]-[1,2,4]triazolo[1,5-a]pyridin-2-amine;
or a pharmaceutically active acid addition salt thereof, a racemic mixture or its corresponding enantiomers, optical isomers, and stereoisomers thereof.

3. A medicament containing one or more compounds of claim 1, or a pharmaceutically active acid addition salt thereof, a racemic mixture or its corresponding enantiomers, optical isomers, or stereoisomers thereof, and one or more pharmaceutically acceptable excipients.

4. A method for the treatment of a condition selected from: Alzheimer's disease; cerebral amyloid angiopathy; hereditary cerebral hemorrhage with amyloidosis, Dutch-type (HCHWA-D); multi-infarct dementia; dementia pugilistica; and Down syndrome, which method comprises administering to a patient in need thereof an effective amount of a compound of claim 1, or a pharmaceutically active acid addition salt thereof, a racemic mixture or its corresponding enantiomers, optical isomers, or stereoisomers thereof.

5. A process for preparing a compound of formula I as defined in claim 1, which process comprises:
reacting a compound of formula 2B

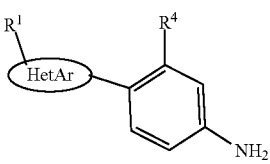

with a compound of formula 3

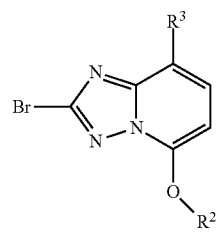

to form a compound of formula I

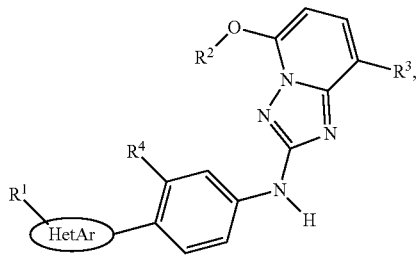

[[IB]] I wherein $R^1$, $R^2$, $R^3$ and $R^4$ are as in claim 1, and, optionally converting the compounds obtained into pharmaceutically acceptable acid addition salts.

6. A compound prepared by the process of claim 5.

7. A medicament containing one or more compounds of claim 2, or a pharmaceutically active acid addition salt thereof, a racemic mixture or its corresponding enantiomers, optical isomers, or stereoisomers thereof, and one or more pharmaceutically acceptable excipients.

8. A method for the treatment of a condition selected from: Alzheimer's disease; cerebral amyloid angiopathy; hereditary cerebral hemorrhage with amyloidosis, Dutch-type (HCHWA-D); multi-infarct dementia; dementia pugilistica; and Down syndrome, which method comprises administering to a patient in need thereof an effective amount of a compound of claim 2, or a pharmaceutically active acid addition salt thereof, a racemic mixture or its corresponding enantiomers, optical isomers, or stereoisomers thereof.

* * * * *